United States Patent
Sanghera et al.

(10) Patent No.: US 10,215,768 B2
(45) Date of Patent: Feb. 26, 2019

(54) LIPID BILAYER SENSOR SYSTEM

(71) Applicant: Oxford Nanopore Technologies Limited, Kidlington (GB)

(72) Inventors: Gurdial Singh Sanghera, Oxford (GB); Steven Paul White, Oxford (GB); Terrence Alan Reid, Bicester (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 14/731,104

(22) Filed: Jun. 4, 2015

(65) Prior Publication Data

US 2015/0268256 A1    Sep. 24, 2015

Related U.S. Application Data

(63) Continuation of application No. 12/527,679, filed as application No. PCT/GB2008/000562 on Feb. 18, 2008.

(30) Foreign Application Priority Data

Feb. 20, 2007 (GB) .................................. 0703256.8
Feb. 20, 2007 (GB) .................................. 0703257.6

(51) Int. Cl.
*G01N 33/92* (2006.01)
*G01N 33/487* (2006.01)

(52) U.S. Cl.
CPC ....... *G01N 33/92* (2013.01); *G01N 33/48728* (2013.01)

(58) Field of Classification Search
CPC ............. G01N 33/92; G01N 33/48728; G01N 33/48721
See application file for complete search history.

(56) References Cited

U.S. PATENT DOCUMENTS 3,799,743 A    3/1974    Aleander et al. ............... 23/253
4,154,795 A    5/1979    Thorne
(Continued)

FOREIGN PATENT DOCUMENTS

CN    1303147 A    7/2001
CN    1434461      8/2003
(Continued)

OTHER PUBLICATIONS

C. Schmidt et al., A Chip-Based Biosensor for the Funtion Analysis of Single Ion Channels, Angew. Chem. Int. Ed., vol. 39. No. 17, pp. 3137-3140 (2000).*
(Continued)

*Primary Examiner* — Maris R Kessel
(74) *Attorney, Agent, or Firm* — Wolf, Greenfield & Sacks, P.C.

(57) ABSTRACT

A sensor system (1) for measuring an electrical signal across a lipid bilayer is formed by a cell (2) and an electrical reader unit (3) which are connectable together. The cell (2) is capable of supporting a lipid bilayer across an aperture (11) in a membrane (10) and has a construction which is cheap to manufacture. The reader unit (3) is a portable device which monitors an electrical signal generated in the connected cell (2) to allow analysis of that electrical signal. The sensor system (1) is intended for use outside of a laboratory setting.

21 Claims, 9 Drawing Sheets

Specification includes a Sequence Listing.

(56) References Cited

U.S. PATENT DOCUMENTS

| | | |
|---|---|---|
| 5,234,566 A | 8/1993 | Osman et al. |
| 5,403,451 A | 4/1995 | Riviello et al. ............ 204/153.1 |
| 6,056,922 A | 5/2000 | Ikematsu ..................... 422/68.1 |
| 6,300,141 B1 | 10/2001 | Segal et al. ................... 436/518 |
| 6,479,288 B1 | 11/2002 | Laffafian et al. ............. 435/455 |
| 6,503,452 B1 | 1/2003 | Boxer et al. ............... 422/82.02 |
| 6,699,697 B2 | 3/2004 | Klemic et al. |
| 6,863,833 B1 | 3/2005 | Bloom et al. ..................... 216/2 |
| 6,913,697 B2 | 7/2005 | Lopez et al. |
| 6,916,488 B1 | 7/2005 | Meier et al. |
| 7,077,939 B1 | 7/2006 | Crooks et al. ................ 204/450 |
| 7,144,486 B1 | 12/2006 | Fritsch et al. |
| 7,169,272 B2 | 1/2007 | Fritsch et al. |
| 7,745,116 B2 | 6/2010 | Williams |
| 7,939,270 B2 | 5/2011 | Holden et al. ................. 435/7.1 |
| 8,124,191 B2 | 2/2012 | Ervin et al. |
| 8,461,854 B2 | 6/2013 | Chen et al. |
| 9,546,400 B2 | 1/2017 | Turner et al. |
| 9,678,056 B2 | 6/2017 | Turner et al. |
| 2002/0123048 A1 | 9/2002 | Gau ................................. 435/6 |
| 2003/0015422 A1 | 1/2003 | Fritsch et al. |
| 2003/0098248 A1 | 5/2003 | Vogel et al. ................ 205/777.5 |
| 2003/0111340 A1 | 6/2003 | Cheng et al. ............. 204/275.1 |
| 2004/0171169 A1 | 9/2004 | Kallury et al. |
| 2005/0014162 A1 | 1/2005 | Barth et al. |
| 2005/0230272 A1 | 10/2005 | Lee et al. |
| 2006/0163063 A1 | 7/2006 | Picollet-Dahan et al. |
| 2007/0035308 A1 | 2/2007 | Ide ............................... 324/439 |
| 2008/0254995 A1 | 10/2008 | Kim et al. |
| 2009/0167288 A1 | 7/2009 | Reid et al. |
| 2010/0147450 A1 | 6/2010 | Takeuchi et al. |
| 2010/0190253 A1 | 7/2010 | Tazaki et al. |
| 2010/0304980 A1 | 12/2010 | Takeuchi et al. |
| 2011/0120871 A1 | 5/2011 | Reid et al. |
| 2011/0121840 A1 | 5/2011 | Sanghera et al. |
| 2011/0214991 A1 | 9/2011 | Kim et al. |
| 2011/0287414 A1 | 11/2011 | Chen et al. |
| 2012/0010085 A1 | 1/2012 | Rava et al. |
| 2013/0071932 A1 | 3/2013 | Itchoda et al. |
| 2013/0140192 A1 | 6/2013 | Behrends et al. |
| 2014/0255921 A1 | 9/2014 | Moysey et al. |
| 2014/0296083 A1 | 10/2014 | Brown et al. |
| 2014/0329693 A1 | 11/2014 | Reid et al. |
| 2014/0335512 A1 | 11/2014 | Moysey et al. |
| 2014/0346059 A1 | 11/2014 | Akeson |
| 2015/0014160 A1 | 1/2015 | Hyde et al. |
| 2015/0065354 A1 | 3/2015 | Moysey et al. |
| 2015/0191709 A1 | 7/2015 | Heron et al. |
| 2015/0218629 A1 | 8/2015 | Heron et al. |
| 2015/0265994 A1 | 9/2015 | Hyde et al. |
| 2015/0300986 A1 | 10/2015 | Reid et al. |
| 2016/0040230 A1 | 2/2016 | Akeson |
| 2016/0257942 A1 | 9/2016 | Bruce et al. |
| 2017/0326550 A1 | 11/2017 | Brown et al. |
| 2017/0363577 A1 | 12/2017 | Reid et al. |

FOREIGN PATENT DOCUMENTS

| | | | |
|---|---|---|---|
| CN | 101078704 | 11/2007 | |
| CN | 101490277 A | 7/2009 | |
| CN | 203466320 U | 9/2013 | |
| DE | 102010022929 A1 | 12/2011 | |
| EP | 0532215 A2 | 3/1993 | |
| EP | 1120469 A2 | 8/2001 | |
| EP | 1669746 | 6/2006 | ............ G01N 27/26 |
| EP | 1677102 | 7/2006 | ............ G01N 27/28 |
| EP | 1688742 | 8/2006 | ............ G01N 33/50 |
| EP | 1710578 | 10/2006 | ........... G01N 33/487 |
| EP | 1712909 | 10/2006 | ............ G01N 33/48 |
| EP | 1779921 A1 | 5/2007 | |
| EP | 2219032 A1 | 8/2010 | |
| GB | 2237390 | 5/1991 | |
| GB | 2446823 | 8/2008 | |
| JP | S5-274882 A | 6/1977 | |
| JP | 4014773 A2 | 1/1992 | |
| JP | 4127066 A2 | 4/1992 | |
| JP | 4-215052 | 8/1992 | |
| JP | 7307172 A2 | 11/1995 | |
| JP | 2004-158330 A2 | 6/2004 | |
| JP | 2005-98718 | 4/2005 | |
| JP | 2005-539242 | 12/2005 | |
| JP | 2006-312141 | 11/2006 | |
| JP | 2008-194573 | 8/2008 | |
| JP | 2009-128206 A | 6/2009 | |
| JP | 2010186677 A2 | 8/2010 | |
| WO | 94/25862 | 11/1994 | ........... G01N 27/333 |
| WO | WO 1997/016545 A1 | 5/1997 | |
| WO | 98/58248 | 12/1998 | ........... G01N 27/327 |
| WO | 00/25121 | 5/2000 | ........... G01N 27/327 |
| WO | 00/28312 | 5/2000 | ............ G01N 27/26 |
| WO | 02/24862 | 3/2002 | .............. C12M 1/34 |
| WO | 02/29402 | 4/2002 | ............ G01N 33/00 |
| WO | WO 2002/035221 A1 | 5/2002 | |
| WO | 02/082046 | 10/2002 | |
| WO | WO 2003/052420 A2 | 6/2003 | |
| WO | WO 2005/040783 A1 | 5/2005 | |
| WO | WO 2006/012571 A1 | 2/2006 | |
| WO | WO 2006/076703 A2 | 7/2006 | |
| WO | 2006/100484 | 9/2006 | |
| WO | 2006/104639 | 10/2006 | ............. H01L 51/44 |
| WO | 2006/113550 | 10/2006 | ............... C12Q 1/70 |
| WO | WO 2006/138160 A2 | 12/2006 | |
| WO | WO 2007/028003 A2 | 3/2007 | |
| WO | WO 2007/049576 A1 | 5/2007 | |
| WO | WO 2007/116978 A1 | 10/2007 | |
| WO | 2007/127327 | 11/2007 | .............. B01J 13/02 |
| WO | WO 2007/132002 A1 | 11/2007 | |
| WO | WO 2008/012552 A1 | 1/2008 | |
| WO | WO 2008/054611 A2 | 5/2008 | |
| WO | WO 2008/102120 | 8/2008 | |
| WO | WO 2008/102121 | 8/2008 | |
| WO | WO 2008/124107 A1 | 10/2008 | |
| WO | WO 2008/156041 A1 | 12/2008 | |
| WO | WO 2009/024775 A1 | 2/2009 | |
| WO | WO 2009/035647 A1 | 3/2009 | |
| WO | WO 2009/077734 A2 | 6/2009 | |
| WO | WO 2010/122293 | 10/2010 | |
| WO | WO 2010/142954 A1 | 12/2010 | |
| WO | WO 2011/118211 A1 | 9/2011 | |
| WO | WO 2011/154114 A2 | 12/2011 | |
| WO | WO 2013/153359 A1 | 10/2013 | |
| WO | WO 2014/013260 A1 | 1/2014 | |
| WO | WO 2014/064443 A2 | 5/2014 | |
| WO | WO 2014/064444 A1 | 5/2014 | |
| WO | WO 2014/158665 A1 | 10/2014 | |

OTHER PUBLICATIONS

Krantz Lab, "Planar Lip Bilayer Electrohpysiology Equipment", Department of Molecular & Cell Biology, University of California, Berkeley, <mcb.berkeley.edu/labs/kranlz/equipment/blm.html>, Sep. 8, 2006 (last accessed Dec. 19, 2016).*

Avanti Polar Lipids, Inc.; "Avanti Polar Lipids—Preparations of Liposomes"; www.avantilipids.com; pp. 5, Jul. 1, 2014.

Lee et al., "Ion channel switch array: A biosensor for detecting multiple pathogens", Industrial Biotechnology, Spring 2005, 7 pages.

Lewis et al, "The Mesomorphic Phase Behavior of Lipid Bilayers", The Structure of Biological Membranes, Second Edition, 19 pages, 2005.

Schindler et al., Branched Bimolecular Lipid Membranes, Biophysical Journal, 16, p. 1109-1113, 1976.

Li et al.; "Printing via Photolithograohy on Micropartitioned Fluid Lipid Membranes"; Adv. Mater., vol. 12, No. 10; pp. 731-734, 2000.

McAlduff et al.; "Freestanding Lipid Bilayers as Substrates for Electron Cryomicroscopy of Intergral Membrane Proteins"; Journal of Microscopy, vol. 205, Pt. 2; pp. 113-117, 2002.

Estes et al.; "Electroformation of Giant Liposomes from Spin-coated Films of Lipids"; Colloids and Surfaces B: Biointerfaces, vol. 42; pp. 115-153, 2005.

Majd et al.; "Hydrogel Stamping of Arrays of Supported Lipid Bilayers with Various Lipid Compositiotns for the Screening of

(56) References Cited

OTHER PUBLICATIONS

Drug-Membrane and Protein-Membrane Interactions"; Angew. Chem. Int. Ed. , vol. 44; pp. 6697-6700, 2005.
Moran-Mirabal et al.; "Micrometer-Sized Support Lipid Bilayer Arrays for Bacterial Toxin Binding Studies Through Total Internal Reflection Fluorescence Microscopy"; Biophysical Journal, vol. 89; pp. 296-305, 2005.
Parthasarathy et al.; "Protein Patterns at Lipid Bilayer Junctions"; PNAS, vol. 101, No. 35; pp. 12798*12803, Aug. 31, 2004.
Kam et al.; "Spatially Selective Manipulation of Supported Lipid Bilayers by Laminar Flow: Step Toward Biomembrane Microfluidics"; Langmuir, vol. 19; pp. 1624-1631, 2003.
Hovis et al.; "Patterning and Composition Arrays of Support Lipid Bilayers by Microcontact Printing"; Langmuir, vol. 17; pp. 3400-3405, 2001.
Maurer et al.; "Reconstruction of Ion Channels in Agarose-Supported Silicon Orifices"; Biosensors and Bioelectronics, vol. 22; pp. 2577-2584, 2007.
Schmidt et al.; "A Chip-Based Biosensor for the Functional Analysis of Single Ion Channels"; Angew. Chem. Int. Ed., vol. 39, No. 17; pp. 4, 2000.
Bezrukov et al.; "Counting Polymers Moving Through a Single Ion Channel"; Letters to Nature, vol. 370; pp. 3, Jul. 28, 1994.
Montal et al.; "Formation of Biomolecular Membranes from Lipid Monolayers and a Study of Their Electrical Properties"; Proc. Nat. Acad. Sci. USA, vol. 69, No. 12; pp. 3561-3566, Dec. 1972.
Römer et al.; "Impedance Analysis and Single-Channel Recordings on Nano-Black Lipid Membranes Based on Porous Alumina"; Biophysical Journal, vol. 86; pp. 955-965, Feb. 2004.
Kasianowicz et al.; "Protonation Dynamics of the α-Toxin Ion Channel from Spectral Analysis of pH-Dependent Current Fluctuations"; Biophysical Journal, vol. 69; pp. 94-105, Jul. 1995.
Suzuki et al.; "Highly Reproducible Method of Planar Lipid Bilayer Reconstitution in Polymethyl Methacrylate Microfluidic Chip"; Langmuir, vol. 22, No. 4; pp. 1937-1942, 2006.
Suzuki et al.; "Planar Lipid Bilayer Reconstitution with a Micro-Fluidic System"; Lab on a Chip, vol. 14; pp. 4, Jan. 2004.
Shim et al.; "Stochastic Sensing on a Modular Chip Containing a Single-Ion Channel"; Anal. Chem., vol. 79, No. 6; pp. 2207-2213, Mar. 15, 2007.
Rauf et al.; "Studies on Sildenafil Citrate (Viagra) Interaction With DNA Using Electrochemical DNA Biosensor"; Biosensors and Bioelectronics, vol. 22; pp. 2471-2477, 2007.
International Search Report; PCT/GB2008/000562; pp. 4, dated Jun. 12, 2008.
International Search Report; PCT/GB2008/000563; pp. 3, dated Jun. 5, 2008.
International Preliminary Report on Patentability; PCT/GB2008/000563; pp. 7, dated Sep. 3, 2009.
International Preliminary Report on Patentability; PCT/GB2008/000562; pp. 8, dated Sep. 3, 2009.
Krantz Lab, "Planar Lip Bilayer Electrohpysiology Equipment", Department of Molecular & Cell Biology, University of California, Berkeley, <mcb.berkeley.edu/labs/krantz/equipment/blm.html>, Oct. 6, 2007 (last accessed Nov. 26, 2014).
Aghdaei et al., Formation of artificial lipid bilayers using droplet dielectrophoresis. Lab Chip. Oct. 2008;8(10):1617-20. doi: 10.1039/b807374k. Epub Aug. 13, 2008.
Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.
Anrather et al., Supported membrane nanodevices. J Nanosci Nanotechnol. Jan.-Feb. 2004;4(1-2):1-22.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.
Bruggemann et al., Microchip technology for automated and parallel patch-clamp recording. Small. Jul. 2006;2(7):840-6.
Cheng et al., Discrete membrane arrays. J Biotechnol. Sep. 2000;74(3):159-74.
Cheng et al., Single Ion Channel Sensitivity in Suspended Bilayers on Micromachined Supports. Langmuir. 2001;17(4):1240-1242.
Danelon et al., Cell membranes suspended across nanoaperture arrays. Langmuir. Jan. 3, 2006;22(1):22-5.
Devereux et al., A comprehensive set of sequence analysis programs for the VAX. Nucleic Acids Res. Jan. 11, 1984;12(1 Pt 1):387-95.
Funakoshi et al., Lipid bilayer formation by contacting monolayers in a microfluidic device for membrane protein analysis. Anal Chem. Dec. 15, 2006;78(24):8169-74.
Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.
Heron et al., Simultaneous measurement of ionic current and fluorescence from single protein pores. J Am Chem Soc. Feb. 11, 2009;131(5):1652-3. doi: 10.1021/ja808128s.
Hirano et al., Lipid Bilayers at Gel/Gel Interface for Ion Channel Recordings. Surf. Sci. Nanotech. 2008;6:130-133.
Holden et al., Functional bionetworks from nanoliter water droplets. J Am Chem Soc. Jul. 11, 2007;129(27):8650-5. Epub Jun. 16, 2007.
Hromada et al., Single molecule measurements within individual membrane-bound ion channels using a polymer-based bilayer lipid membrane chip. Lab Chip. Apr. 2008;8(4):602-8. doi:10.1039/b716388f. Epub Feb. 29, 2008.
Ide et al., A novel method for artificial lipid-bilayer formation. Biosens Bioelectron. Oct. 15, 2005;21(4):672-7. Epub Jan. 26, 2005.
Jeon et al., Long-term storable and shippable lipid bilayer membrane platform. Lab Chip. Oct. 2008;8(10):1742-4. doi: 10.1039/6807932c. Epub Aug. 22, 2008.
Jung et al., Detecting protein-ligand binding on supported bilayers by local pH modulation. J Am Chem Soc. Jan. 28, 2009;131(3):1006-14. doi: 10.1021/ja804542p.
Khafizov, Single Molecule Force Spectroscopy of Single Stranded Dna Binding Protein and Rep Helicase. University of Illinois at Urbana-Champaign Dissertation. 2012.
Kim et al., Liquid-slate field-effect transistors using electrowetting. Applied Physics Letters. Jan. 22, 2007;90(4):043507-1-043507-3.
Korolev et al., Major domain swiveling revealed by the crystal structures of complexes of E. coli Rep heilcase bound to single-stranded DNA and ADP. Cell. Aug. 22, 1997;90(4):635-47.
Le Pioufle et al., Lipid bilayer microarray for parallel recording of transmembrane ion currents. Anal Chem. Jan. 1, 2008;80(1):328-32. Epub Nov. 15, 2007.
Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.
Lee et al., Polyelectrolyte Micropatterning Using Agarose Plane Stamp and a Substrate Having Microscale Features on Its Surface. Bull. Korean Chem. Soc., vol. 26(10):1539-1542 (2005).
Li et al., Microfluidic system for planar patch clamp electrode arrays. Nano Lett. Apr. 2006;6(4):815-9.
Mach et al., Miniaturized planar lipid bilayer: increased stability, low electric noise and fast fluid perfusion. Anal Bioanal Chem. Feb. 2008;390(3):841-6. Epub Oct. 31, 2007.
Malmstadt et al., Automated formation of lipid-bilayer membranes in a microfluidic device. Nano Lett. Sep. 2006;6(9):1961-5.
Mangold et al., Reference electrodes based on conducting polymers. Fresenius J Anal Chem. Jun. 2000;367(4):340-2.
Ogier et al., "Suspended Planar Phospholipid Bilayers on Micromachined Supports," Langmuir, vol. 16:5696-5701 (2000).
Peterman et al., "Ion Channels and Lipid Bilayer Membranes Under High Potentials Using Microfabricaled Apertures," Biomedical Microdevices, vol. 4(3):231-236 (2002).

(56) References Cited

OTHER PUBLICATIONS

Polk et al., "Ag/AgCl microelectrodes with improved stability for microfluidics," Sensors and Actuators B., vol. 114:239-247 (2006).
Sackmann, Supported membranes: scientific and practical applications. Science. Jan. 5, 1996;271(5245):43-8.
Sandison et al., "Rapid fabrication of polymer microfluidic systems for the production of artificial lipid bilayers," J. Micromelh. Microeng., vol. 15:S139-S144 (2005).
Sandison et al., Air-exposure technique for the formation of artificial lipid bilayers in microsystems. Langmuir. Jul. 17, 2007;23(15):8277-84. Epub Jun. 22, 2007.
Sapra et al., Lipid-coated hydrogel shapes as components of electrical circuits and mechanical devices. Sci Rep. 2012;2:848. doi: 10.1038/srep00848. Epub Nov. 14, 2012.
Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sun et al., Microfluidic static droplet arrays with tuneable gradients in material composition. Lab Chip. Dec. 7, 2011;11(23):3949-52. doi: 10.1039/c1lc20709a. Epub Oct. 12, 2011.
Suzuki et al., Planar Lipid Membrane Array for Membrane Protein Chip. 17th IEEE International Conference on Micro Electro Mechanical Systems (MEMS), pp. 272-275 (2004).
Thorsen et al., Dynamic pattern formation in a vesicle-generating microfluidic device. Phys Rev Lett. Apr. 30, 2001;86(18):4163-6.
Urisu et al., Formation of high-resistance supported lipid bilayer on the surface of a silicon substrate with microelectrodes. Nanomedicine. Dec. 2005;1(4):317-22.
Vulto et al., Microfluidic channel fabrication in dry film resist for production and prototyping of hybrid chips. Lab Chip. Feb. 2005;5(2):158-62. Epub Dec. 3, 2004.
Wagterveld et al., Ultralow hysteresis superhydrophobic surfaces by excimer laser modification of SU-8. Langmuir. Dec. 19, 2006;22(26):10904-8.
Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.
Zagnoni et al., Controlled delivery of proteins into bilayer lipid membranes on chip. Lab Chip. Sep. 2007;7(9):1176-83. Epub Jun. 27, 2007.
Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.
Hasanzadeh et al., Room-temperature ionic liquid-based electrochemical nanobiosensors. Trends Anal Chem. Dec. 2012;41:58-74.
Langecker et al., Synthetic lipid membrane channels formed by designed DNA nanostructures. Science. Nov. 16, 2012;338(6109):932-6. doi: 10.1126/science.1225624.
Mastrangeli et al., Challenges for Capillary Self-Assembly of Microsystems. IEEE Transactions. Jan. 2011;1(1):133-149.
Mastrangeli et al., Self-assembly from milli- to nanoscales:methods and applications. J Micro Microeng. 2009;19:083001.
Onoe et al., Three-Dimensional Micro-Self-Assembly Using Hydrophobic Interaction Controlled by Self-Assembled Monolayers. J Micro Systems. Aug. 2004;13(4):603-611.
Smith et al., Micropatterned fluid lipid bilayer arrays created using a continuous flow microspotter. Anal Chem. Nov. 1, 2008;80(21):7980-7. doi: 10.1021/ac800860u. Epub Oct. 8, 2008.
Soni et al., Synchronous optical and electrical detection of biomolecules traversing through solid-state nanopores. Rev Sci Instrum. Jan. 2010;81(1):014301. doi: 10.1063/1.3277116.
Syms et al., Surface Tension-Powered Self-Assembly of Microstructures—The State of the Art. J Micro Systems. Aug. 2003;12(4):387-417.

\* cited by examiner

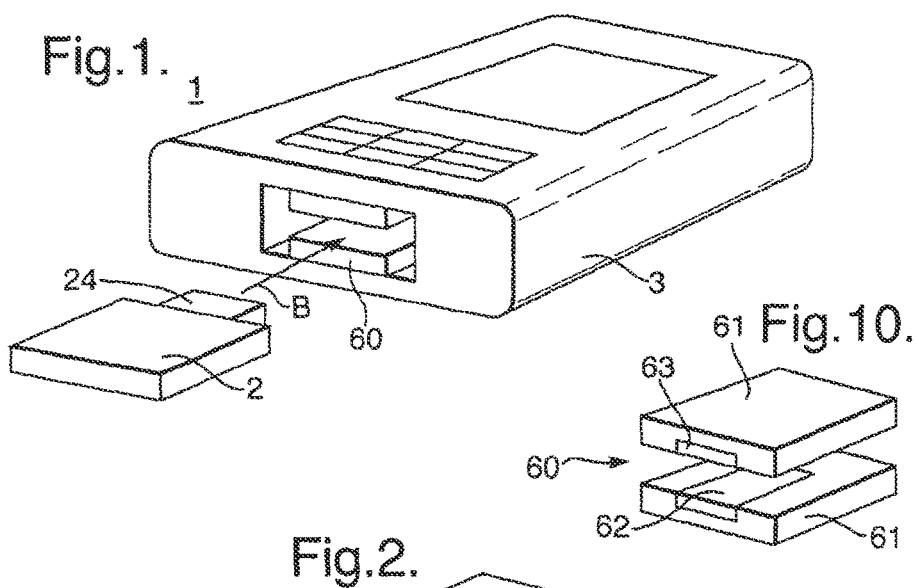
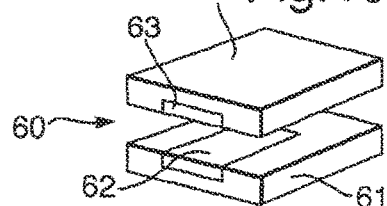
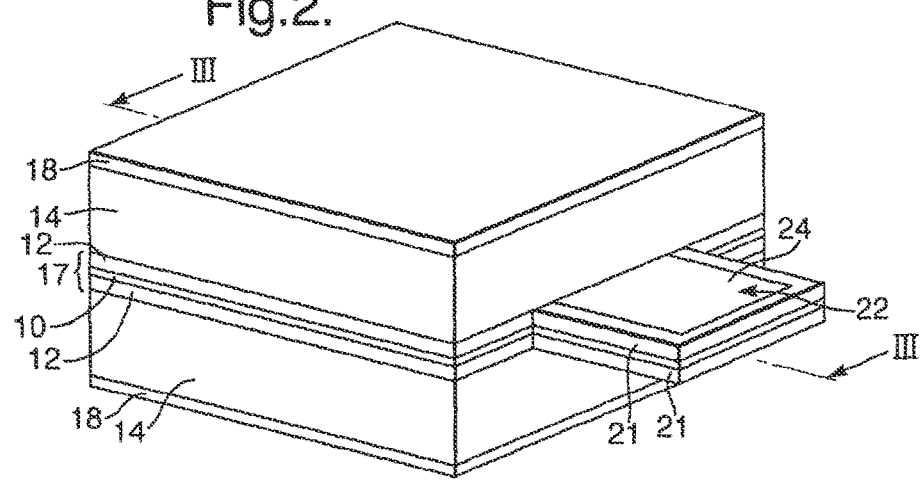
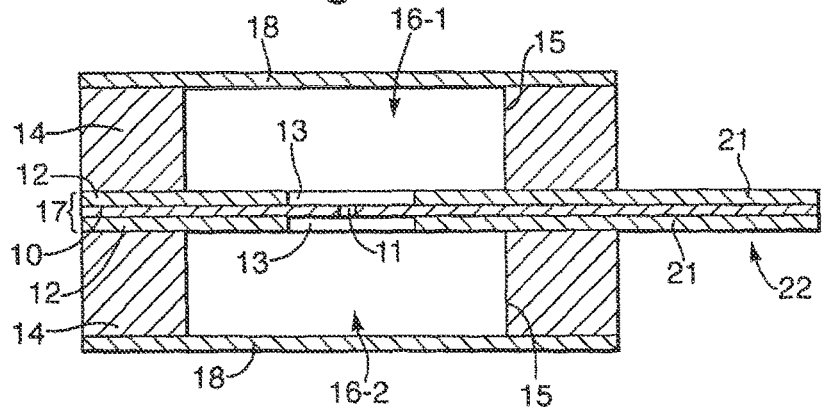

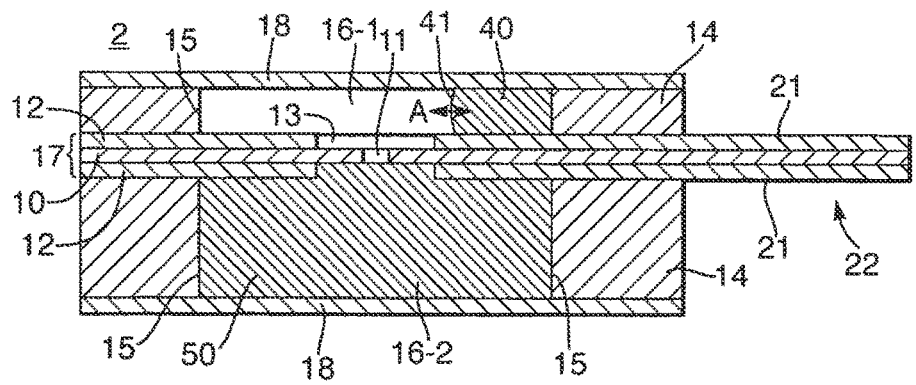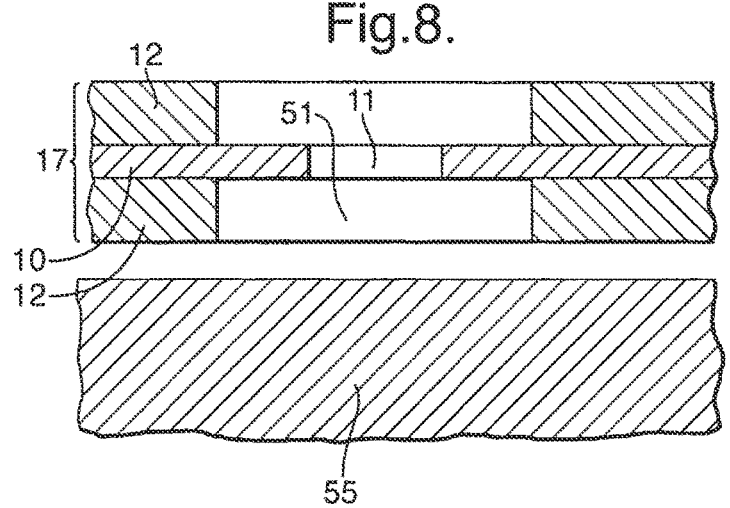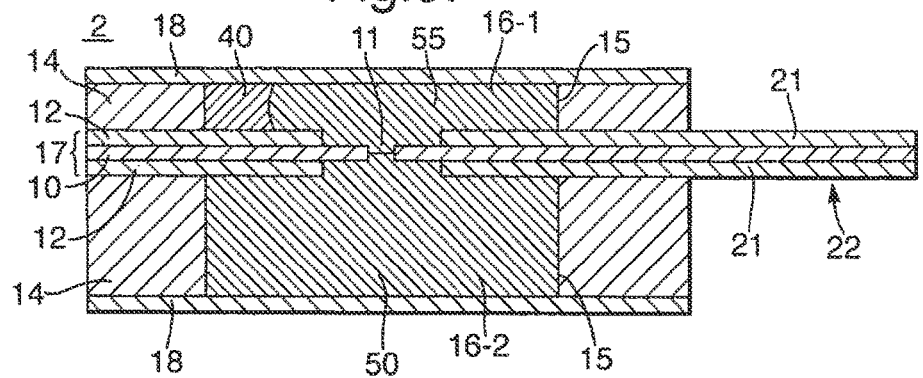

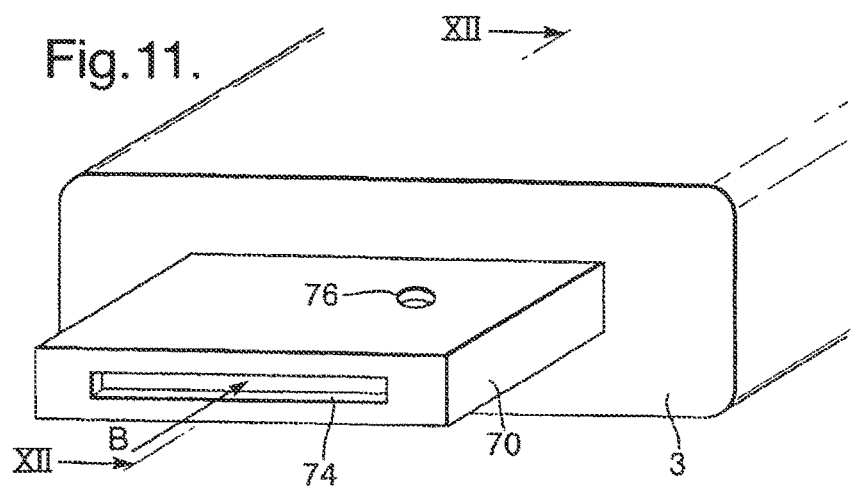
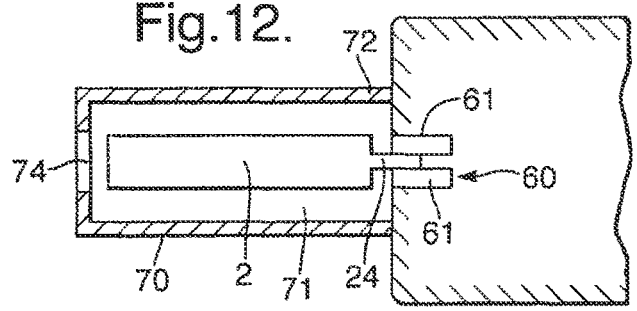
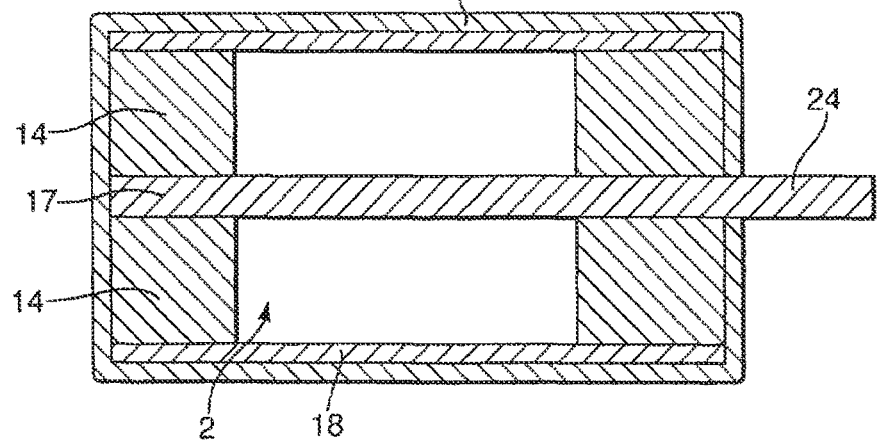

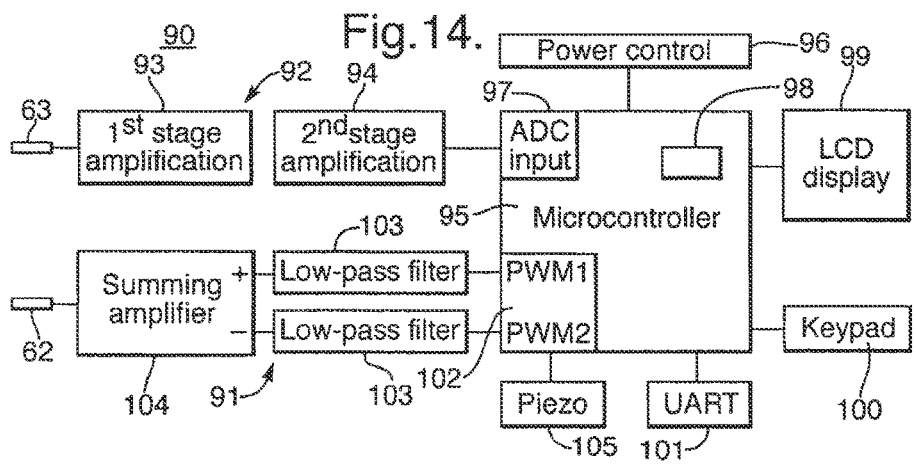
Fig. 14.
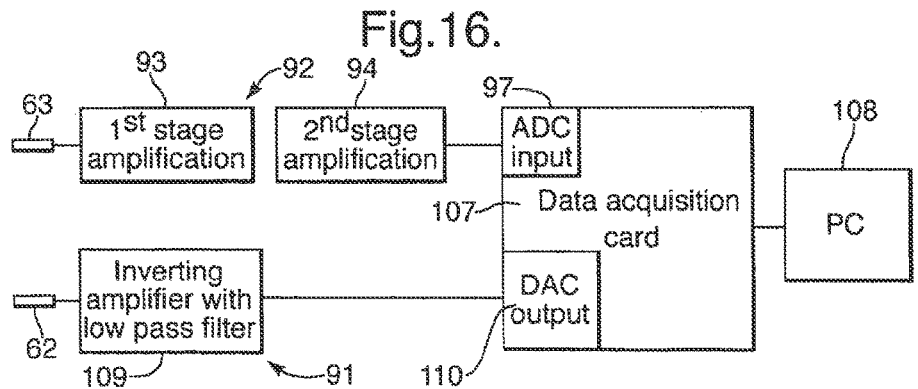
Fig. 15.
Fig. 16.

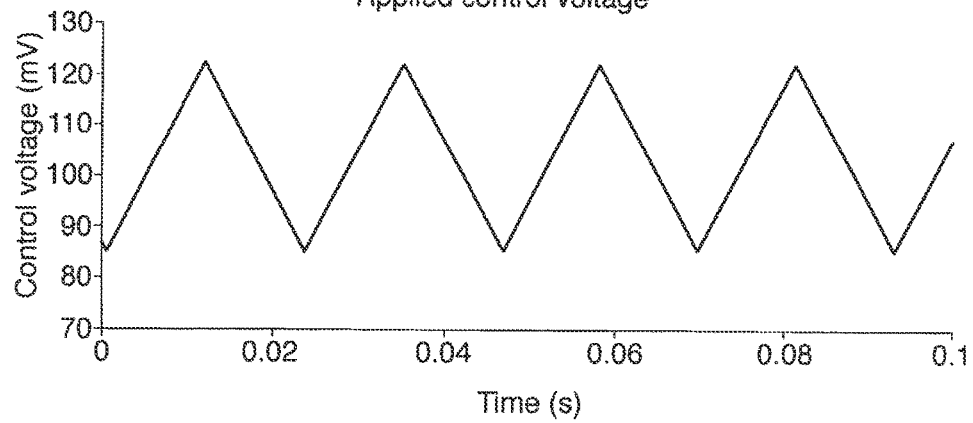
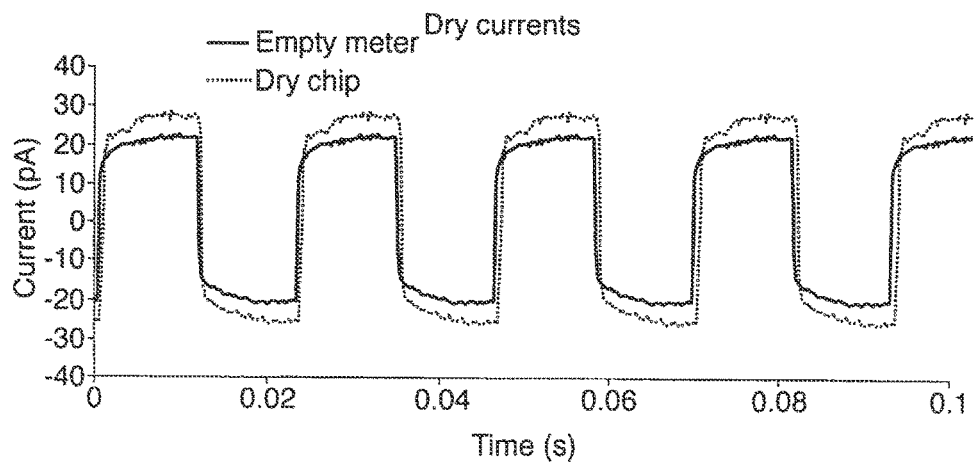

No bilayer: open aperture current

Bilayer current

Pore Insertion

Analyte binding

SEQUENCE LISTING

<160> NUMBER OF SEQ ID NOS: 3

<210> SEQ ID NO 1
<211> LENGTH: 960
<212> TYPE: DNA
<213> ORGANISM: Staphylococcus aureus
<220> FEATURE:
<221> NAME/KEY: CDS
<222> LOCATION: (1)..(960)

<400> SEQUENCE: 1

```
atg aaa aca cgt ata gtc agc tca gta aca aca aca cta ttg cta ggt      48
Met Lys Thr Arg Ile Val Ser Ser Val Thr Thr Thr Leu Leu Leu Gly
1               5                   10                  15 tcc ata tta atg aat cct gtc gct aat gcc gca gat tct gat att aat      96
Ser Ile Leu Met Asn Pro Val Ala Asn Ala Ala Asp Ser Asp Ile Asn
            20                  25                  30 att aaa acc ggt act aca gat att gga agc aat act aca gta aaa aca    144
Ile Lys Thr Gly Thr Thr Asp Ile Gly Ser Asn Thr Thr Val Lys Thr
        35                  40                  45 ggt gat tta gtc act tat gat aaa gaa aat ggc atg cac aaa aaa gta    192
Gly Asp Leu Val Thr Tyr Asp Lys Glu Asn Gly Met His Lys Lys Val
    50                  55                  60
```

```
ttt tat agt ttt atc gat gat aaa aat cac aat aaa aaa ctg cta gtt      240
Phe Tyr Ser Phe Ile Asp Asp Lys Asn His Asn Lys Lys Leu Leu Val
 65                  70                  75                  80 att aga aca aaa ggt acc att gct ggt caa tat aga gtt tat agc gaa      288
Ile Arg Thr Lys Gly Thr Ile Ala Gly Gln Tyr Arg Val Tyr Ser Glu
                 85                  90                  95 gaa ggt gct aac aaa agt ggt tta gcc tgg cct tca gcc ttt aag gta      336
Glu Gly Ala Asn Lys Ser Gly Leu Ala Trp Pro Ser Ala Phe Lys Val
            100                 105                 110 cag ttg caa cta cct gat aat gaa gta gct caa ata tct gat tac tat      384
Gln Leu Gln Leu Pro Asp Asn Glu Val Ala Gln Ile Ser Asp Tyr Tyr
        115                 120                 125 cca aga aat tcg att gat aca aaa gag tat atg agt act tta act tat      432
Pro Arg Asn Ser Ile Asp Thr Lys Glu Tyr Met Ser Thr Leu Thr Tyr
    130                 135                 140 gga ttc aac ggt aat gtt act ggt gat gat aca gga aaa att ggc ggc      480
Gly Phe Asn Gly Asn Val Thr Gly Asp Asp Thr Gly Lys Ile Gly Gly
145                 150                 155                 160 ctt att ggt gca aat gtt tcg att ggt cat aca ctg aaa tat gtt caa      528
Leu Ile Gly Ala Asn Val Ser Ile Gly His Thr Leu Lys Tyr Val Gln
                165                 170                 175 cct gat ttc aaa aca att tta gag agc cca act gat aaa aaa gta ggc      576
Pro Asp Phe Lys Thr Ile Leu Glu Ser Pro Thr Asp Lys Lys Val Gly
            180                 185                 190 tgg aaa gtg ata ttt aac aat atg gtg aat caa aat tgg gga cca tac      624
Trp Lys Val Ile Phe Asn Asn Met Val Asn Gln Asn Trp Gly Pro Tyr
        195                 200                 205 gat cga gat tct tgg aac ccg gta tat ggc aat caa ctt ttc atg aaa      672
Asp Arg Asp Ser Trp Asn Pro Val Tyr Gly Asn Gln Leu Phe Met Lys
    210                 215                 220 act aga aat ggt tct atg aaa gca gca gat aac ttc ctt gat cct aac      720
Thr Arg Asn Gly Ser Met Lys Ala Ala Asp Asn Phe Leu Asp Pro Asn
225                 230                 235                 240 aaa gca agt tct cta tta tct tca ggg ttt tca cca gac ttc gct aca      768
Lys Ala Ser Ser Leu Leu Ser Ser Gly Phe Ser Pro Asp Phe Ala Thr
                245                 250                 255 gtt att act atg gat aga aaa gca tcc aaa caa caa aca aat ata gat      816
Val Ile Thr Met Asp Arg Lys Ala Ser Lys Gln Gln Thr Asn Ile Asp
            260                 265                 270 gta ata tac gaa cga gtt cgt gat gat tac caa ttg cat tgg act tca      864
Val Ile Tyr Glu Arg Val Arg Asp Asp Tyr Gln Leu His Trp Thr Ser
        275                 280                 285 aca aat tgg aaa ggt acc aat act aaa gat aaa tgg aca gat cgt tct      912
Thr Asn Trp Lys Gly Thr Asn Thr Lys Asp Lys Trp Thr Asp Arg Ser
    290                 295                 300 tca gaa aga tat aaa atc gat tgg gaa aaa gaa gaa atg aca aat taa      960
Ser Glu Arg Tyr Lys Ile Asp Trp Glu Lys Glu Glu Met Thr Asn
305                 310                 315
```

<210> SEQ ID NO 2
<211> LENGTH: 319
<212> TYPE: PRT
<213> ORGANISM: Staphylococcus aureus

<400> SEQUENCE: 2

```
Met Lys Thr Arg Ile Val Ser Ser Val Thr Thr Thr Leu Leu Leu Gly
  1               5                  10                  15

Ser Ile Leu Met Asn Pro Val Ala Asn Ala Ala Asp Ser Asp Ile Asn
             20                  25                  30
```

```
Ile Lys Thr Gly Thr Thr Asp Ile Gly Ser Asn Thr Thr Val Lys Thr
             35                  40                  45

Gly Asp Leu Val Thr Tyr Asp Lys Glu Asn Gly Met His Lys Lys Val
 50                  55                  60

Phe Tyr Ser Phe Ile Asp Asp Lys Asn His Asn Lys Lys Leu Leu Val
 65                  70                  75                  80

Ile Arg Thr Lys Gly Thr Ile Ala Gly Gln Tyr Arg Val Tyr Ser Glu
                 85                  90                  95

Glu Gly Ala Asn Lys Ser Gly Leu Ala Trp Pro Ser Ala Phe Lys Val
                100                 105                 110

Gln Leu Gln Leu Pro Asp Asn Glu Val Ala Gln Ile Ser Asp Tyr Tyr
                115                 120                 125

Pro Arg Asn Ser Ile Asp Thr Lys Glu Tyr Met Ser Thr Leu Thr Tyr
    130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
                180                 185                 190

Trp Lys Val Ile Phe Asn Asn Met Val Asn Gln Asn Trp Gly Pro Tyr
    195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
                260                 265                 270

Val Ile Tyr Glu Arg Val Arg Asp Asp Tyr Gln Leu His Trp Thr Ser
                275                 280                 285

Thr Asn Trp Lys Gly Thr Asn Thr Lys Asp Lys Trp Thr Asp Arg Ser
    290                 295                 300

Ser Glu Arg Tyr Lys Ile Asp Trp Glu Lys Glu Glu Met Thr Asn
305                 310                 315

<210> SEQ ID NO 3
<211> LENGTH: 294
<212> TYPE: PRT
<213> ORGANISM: Staphylococcus aureus

<400> SEQUENCE: 3

Met Ala Asp Ser Asp Ile Asn Ile Lys Thr Gly Thr Thr Asp Ile Gly
  1               5                  10                  15

Ser Asn Thr Thr Val Lys Thr Gly Asp Leu Val Thr Tyr Asp Lys Glu
                 20                  25                  30

Asn Gly Met His Lys Lys Val Phe Tyr Ser Phe Ile Asp Asp Lys Asn
             35                  40                  45

His Asn Lys Lys Leu Leu Val Ile Arg Thr Lys Gly Thr Ile Ala Gly
 50                  55                  60

Gln Tyr Arg Val Tyr Ser Glu Glu Gly Ala Asn Lys Ser Gly Leu Ala
 65                  70                  75                  80

Trp Pro Ser Ala Phe Lys Val Gln Leu Gln Leu Pro Asp Asn Glu Val
                 85                  90                  95
```

```
Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
        130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
            195                 200                 205

Asp Asn Phe Leu Asp Pro Asn Lys Ala Ser Ser Leu Leu Ser Ser Gly
            210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
            275                 280                 285

Lys Glu Glu Met Thr Asn
290
```

LIPID BILAYER SENSOR SYSTEM

RELATED APPLICATION

This application is a continuation of U.S. patent application Ser. No. 12/527,679 filed Aug. 18, 2009; which is a U.S. national stage application of International Application No. PCT/GB2008/000562 filed Feb. 18, 2008, which designates the United States of America, and claims the benefit of Great Britain Patent Application 0703257.6 filed Feb. 20, 2007, now Great Britain Patent 2446823, and Great Britain Patent Application 0703256.8 filed Feb. 20, 2007, now Great Britain Patent 2447043, the contents of which are incorporated herein in their entirety by reference.

The present invention relates to sensor systems for sensing properties of a sample. The present invention is primarily concerned with sensor systems in which in use a lipid bilayer is formed and used for sensing, for example by insertion of a membrane protein and by measurement of an electrical signal developed across the bilayer. However, some aspects of the present invention relate more generally to any type of sensor system.

Many types of sensor systems for sensing properties of a sample are known. Typically these might detect one or more analytes in the sample and/or the magnitude of or changes in physical properties of the sample. One such known type of sensor system uses a lipid bilayer formed across an aperture. Typically, sensing may be achieved by insertion of a membrane protein in the lipid bilayer. An analyte may be sensed using a stochastic sensing technique based on the detection of individual binding events between the analyte and the membrane protein. The membrane protein may be an ion channel in which case the binding event causes a characteristic change in the ionic current across the bilayer, for example under a transmembrane potential. For example, binding sites can be engineered into pores expressly for binding with analytes molecules, which act as partial channel blockers. In this way measurement of an electrical signal developed across the bilayer provides sensing of the analyte.

Sensitive detection of the analyte is difficult unless analyte binding to the membrane protein causes a significant change in electrical conductance between the electrodes relative to the total overall conductance between the electrodes. This means that the majority of the conductance between the electrodes will be through the membrane protein and the analyte binding will significantly interrupt this conductance. In practice this has been best achieved by creating an aperture between two chambers, sealing the aperture using a lipid bilayer, and then inserting the membrane protein into the bilayer. The lipid bilayer forms a reproducible, high resistance, self-healing electrical seal that is thin enough to be breached by the membrane protein. Ionic conductivity between the two compartments is therefore re-established by insertion of transmembrane pores into the bilayer, creating ion conducting channels through the bilayer.

Similarly measurement of an electrical signal or other physical property may provide sensing of other phenomena associated with the lipid bilayer.

Much scientific study of stochastic sensing has been carried out. Indeed, laboratory protein reconstitution studies, such as ion channel measurements, have been performed using such artificial lipid bilayers for several decades. However, this work has been in a laboratory using bulky equipment requiring a user to have a relatively high user skill level and access to complex equipment and chemicals.

Lipid bilayers for protein reconstitution studies may be formed by a variety of methods but the method of Montal & Mueller (Proc. Natl. Acad. Sci. USA. (1972), 69, 3561-3566) is popular as a cost-effective and relatively straightforward method of forming good quality lipid bilayers suitable for protein pore insertion. In this method a lipid monolayer is carried on the water/air interface past either side of an aperture which is perpendicular to that interface. Typically, the lipid is added to the surface of the aqueous electrolyte solution by first dissolving it in an organic solvent, a drop of which is then allowed to evaporate on the surface of the aqueous solution on either side of the aperture. Once the organic solvent has been evaporated, the solution/air interfaces are physically moved repeatedly up and down past either side of the aperture until a bilayer is formed.

However, there would be many practical applications for the sensing outside a laboratory setting, for example in medicine for point of care testing (POCT), in environmental protection for a field based test for pollutants, for counter bioterrorism for the detection of explosives and chemical and biological agents at the "point of terror". There is a clear unmet need for portable sensor devices delivering rapid real time information for single molecule detection.

In such settings outside the laboratory, there a number of desirable characteristics for the system. The system should be portable yet robust. Also the system should be straightforward to use, requiring a lower user skill level than the common laboratory equipment. Also for widespread use, the sensing system should be as cheap as possible.

Various aspects of the present invention are directed to a sensor system which is intended for widespread use outside of the laboratory. Different aspects of the invention are directed to providing one or more of the desirable characteristics for such as system discussed above.

According to the first aspect of the present invention, there is provided a sensor system for measuring an electrical signal across a lipid bilayer, the sensor system comprising a cell and an electrical reader unit which are connectable together, wherein the cell defines two chambers separated by a septum, the septum comprising a membrane having an aperture capable of supporting a lipid bilayer and arranged between the chambers, the cell has electrodes formed in each chamber for receiving an electrical signal developed between the chambers, and the electrical reader unit has a reader circuit operative to measure an electrical signal developed between the chambers of the cell the cell and the reader unit are arranged to be connected together to provide electrical connection between the electrodes of the cell and the reader circuit of the electrical reader unit.

Further according to the first aspect of the invention, there may be provided the cell and the reader unit by themselves.

Thus the system comprises a cell and the reader unit may be separately manufactured and connected together for use. The cell incorporates the physical elements used to perform the sensing. The cell provides two chambers separated by a septum providing an aperture to support a lipid bilayer, as well as electrodes to receive the resultant electrical signal. In use a lipid bilayer is formed across the aperture and a sample is introduced into a chamber to perform a sensing technique. For example, a membrane protein may be inserted into the lipid bilayer to perform sensing of an analyte as described above. The reader unit provides a reader circuit for measuring the resultant electrical signal when the cell is attached thereto.

As the cells may be connected to the reader unit, the cells are effectively replaceable. This facilitates the manufacture of relatively cheap cells which may be used in a common reader unit to perform sensing. In fact the cells may be mass produced sufficiently cheaply to make them a disposable product. This makes the sensor system as a whole flexible and adaptable to a wide range of sensing techniques.

Typically, the chambers each have a volume of 0.1 µl to 250 µl. Thus the cells have a small size relative to a conventional laboratory cell, which allows the overall system to be relatively small increasing the portability.

Furthermore, the reader unit may be manufactured as a portable device, for example being battery-powered, which can be easily transported to the site where sensing is required. The reader unit may be provided with sufficient intelligence to properly interpret the electrical signals and provide a clear result, thereby reducing the skill level required by the user to understand the results.

Thus the sensing system of the present invention facilitates the performance in non-laboratory settings of a wide range of stochastic sensing techniques, and indeed any sensing technique using a lipid bilayer.

Advantageously, the cell and the reader unit have respective connector portions arranged to mate for connection together of the cell and the reader unit, the cell has contacts electrically connected to the electrodes, and the electrical reader unit has contacts electrically connected to the reader circuit, the contacts of the cell and the electrical reader unit being arranged to make electrical connection with each other on connection together of the cell and the reader unit.

As the cell and the reader unit are connectable together by means of connecter portions which mate together, for example by being plugged together, this makes it straightforward to connect the cell and reader unit. Thus facilitates the modular design with a separate cell and reader unit.

In some embodiments, the chambers have a depth, in a direction perpendicular to the septum, of at most 3 mm. This has the advantage that when a liquid is introduced into the chamber, the liquid interface with the air in the chamber is held by surface tension across the depth of the chamber so that the liquid is held on one side of the chamber rather than falling under gravity to the lowest level in the chamber. This allows the chamber to be held in any orientation. The liquid interface may be moved past the aperture, for example to form the lipid bilayer, simply by applying positive or negative pressure to the liquid without regard to the orientation of the cell. In particular this contrasts with a conventional laboratory cell in which the septum is held in a vertical orientation and the liquid interface is moved past the aperture by raising and lowering the level of liquid in the chambers. In the context of use in a non-laboratory setting, the ability to use the cell in any orientation has important advantages of increasing the robustness and flexibility of the system and reducing the skill needed by the user.

Advantageously, the aperture has a diameter in at least one dimension which is 20 µm or less. This contrasts with conventional laboratory apparatus in which the diameter of the aperture is typically of the order of 30 µm to 150 µm, as a compromise between increasing the diameter to encourage insertion and reducing the diameter to decrease noise. However, by restricting the diameter of the aperture in at least one dimension, the mechanical stability of the bilayers formed across the aperture has been found to increase with decreasing diameter. This produces several advantages in the context of a sensing system for use in a non-laboratory setting. Firstly, the bilayer is formed more easily, for example with a reduced number of passes of the liquid interface past the aperture. Thus the system is more easily used and the required skill level reduced. Secondly, the increased stability increase the robustness of the bilayer formation. For example, in an actual embodiment having an aperture of 10 µm diameter, the cell could be firmly knocked against a table, or disconnected from the reader unit and carried by hand without rupturing the bilayer. Such robustness is of significant advantage for use of the system outside the controlled environment of a laboratory.

Advantageously, the membrane has a pretreatment effective to increase the affinity of the membrane to a lipid. Such pretreatments provide significant advantage in the context of a sensing system for use in a non-laboratory setting in that the bilayer is formed more easily, for example with a reduced number of passes of the liquid interface past the aperture. Thus the system is more easily used and the required skill level reduced.

In one type of embodiment, one of the chambers contains a gel, for example a hydrogel, which extends across the aperture in the membrane.

The presence of the gel facilitates the formation of the lipid bilayer by physically supporting the bilayer and also results in the formation of a lipid bilayer with increased stability. This provides significant advantage in the context of a sensing system for use in a non-laboratory setting as discussed above with reference to the aperture size. The chamber is typically filled with the gel such that the gel contacts the membrane. However, there can remain a gap between the gel and the membrane provided the gap is sufficiently small that the gel still supports the lipid bilayer, acting through the solution in the gap.

The above discussed features of using a small aperture diameter, a pretreatment and a gel may be used together, in any combination, to particular advantage. In some embodiments incorporating one or more of these features it is possible to form a lipid bilayer across the aperture following a single pass of the liquid interface, thereby removing the need to move the interface back and forth past the aperture. This allows formation of the bilayer simply by the introduction of liquid into a chamber without the need for fluidics control to be provided in the system thereby reducing its cost and size.

Some advantageous features of the reader unit will now be discussed.

In some embodiments, the electrical reader unit further comprises a rigid metal body having a cavity containing the connector portion of the electrical reader unit and being of sufficient size to accommodate a cell when connected to the electrical reader unit, the rigid metal body having an aperture which aperture faces the connector portion of the electrical reader unit and is of sufficient size to allow passage of the cell for connection of the cell to the electrical reader unit.

As the rigid metal body accommodates the cell when connected to the reader unit, it thereby acts as a Faraday cage which reduces electrical interference with the electrical signals generated in the cell from ambient electromagnetic radiation. However rather than completely enclosing the cell, the metal body has an aperture which allows passage of the cell for connection of the cell to the electrical reader unit. This allows the cell to be connected to the reader unit without removal and replacement of the rigid metal body, which simplifies the use of the system. This has been understood to be possible whilst still providing the effect of reducing electrical interference. This is based on an appreciation that the aperture may be of sufficiently small size that the electrical interference which remains is at a high frequency which does not significantly degrade the quality of the electrical signal of interest.

Advantageously, the reader circuit is operative to interpret the electrical signal electrical signal measured thereby by detecting one or more of the following states in the cell and producing an output indicative of the detected state, the states being:

1) the chambers in the cell being dry;
2) the chambers in the cell containing an aqueous solution without a lipid bilayer being formed across the aperture in the membrane;
3) a lipid bilayer being formed across the aperture in the membrane without a membrane protein being inserted therein;
4) a lipid bilayer being formed across the aperture in the membrane with a membrane protein being inserted therein without an analyte binding to the membrane protein; and
5) a lipid bilayer being formed across the aperture in the membrane with a membrane protein being inserted therein with an analyte binding to the membrane protein.

It is an important advantage of the use of membrane proteins in a lipid bilayer as a sensor that the electrical signal developed is characteristic of the state of the physical system. This has been extensively documented in the case of laboratory experiments. However, instead of relying on the user to interpret the meaning of the observed signal, it has been appreciated that the reader unit may do so and produce an output of the detected state. This provides significant advantage in the context of a system for use in a non-laboratory setting because it reduces the required skill level of the user who may monitor the progress of the sensing without needing to understand the electrical signal. This also allows the display requirements of the reader unit to be reduced, which in turn reduces cost, because it is only necessary to display the output indicative of the current state and is not necessary to display the electrical signal in sufficient resolution to allow the user to interpret it.

According to the second aspect of the present invention, there is provided a cell for supporting a lipid bilayer, the cell comprising:

body elements defining two chambers;

a septum separating the two chambers and comprising a membrane having an aperture capable of supporting a lipid bilayer arranged between the chambers the body elements on at least one side of the septum comprising a sheet of material fixed with an inner planar surface facing the septum and defining a said chamber having an opening in said inner planar surface aligned with the aperture in the membrane.

Thus the second aspect of the present invention provides a cell in which sensing using a lipid bilayer may be performed. In use, the lipid bilayer is formed across the aperture and used for sensing, for example by insertion of a membrane protein and by measurement of a resultant electrical signal across the septum as discussed above. The particular construction of the cell provides for cheap manufacture. By defining a chamber in a sheet of material which is fixed against the septum, the cost of manufacture is cheap because the sheet of material is easy to form and affix.

The sheet of material forming part of the cell is easy to manufacture simply by cutting from a larger sheet. In this manner, the sheets for several cells may be made together, thereby reducing processing costs.

Similarly the chamber is easy to form in the sheet, for example by removal of material from the sheet. In one form of embodiment, the chamber is defined by an aperture extending through the sheet, this being particularly easy to form for example by a cutting or punching process.

In many embodiments, the chambers on both sides of the septum are formed by respective sheets of material, although in some embodiments the chamber on one side may be formed by some other form of body element.

Advantageously, the septum comprises, on at least one side of the membrane, a support sheet of lesser thickness than the body element, fixed to the membrane, the support sheet having a window which is of greater size than the aperture in the membrane, is of lesser size than the opening of the chamber defined by the body element on the same side, and is aligned with both the aperture in the membrane and with and the opening of the chamber defined by the body element on the same side.

This construction is advantageous because the support sheet strengthens the membrane. The support sheet extends across at least part of the opening in the sheet of material defining the chamber and therefore supports the membrane in the overlapping area. Nonetheless, as the window in the support sheet is of greater size than the aperture in the membrane, the support sheet does not interfere with the formation of the lipid bilayer across the aperture in the membrane. Furthermore this supporting function is provided whilst retaining a simple layered construction which is straightforward an easy to manufacture.

For a greater degree of strengthening of the membrane, a support sheet may be provided on both sides of the membrane, although this is not essential.

Advantageously, in the case that a said support sheet is provided on the same side of the membrane as said sheet of material, the chamber defined by said sheet of material has therein an electrode deposited on the surface of the support sheet internal to the chamber.

The electrode may be used as one of a pair of electrodes to detect an electrical signal developed across the septum. This particular location for the electrode is advantageous because it is convenient and easy to form the electrode. In particular, the electrode may be formed on the support sheet prior to assembly of the cell, for example by printing.

Advantageously, the support sheet extends beyond the periphery of said sheet of material. In this case the protruding part of the support sheet may form a connector portion for insertion into a mating connector portion of an electrical reader unit. This allows the cell to be connected to the reader unit with a cell having a simple layered construction which is easy to manufacture.

In this case, to provide electrical connection to the reader unit, one advantageous arrangement is for the surface of the support sheet facing the chamber to have deposited thereon a contact on the connector portion and a conductive track electrically connecting the contact and the electrode, for example formed by different portions of a common layer of conductive material.

Advantageously, the chamber is closed except for an inlet formed in the cell for introduction of a sample into the chamber. This contrasts with a conventional laboratory apparatus in which the chambers are formed as recesses open to the atmosphere. Use of a closed chamber has the advantage of reducing evaporation from the contents of the chamber in use. This in turn reduces the cooling of the contents which is important to maintain appropriate temperatures in the case of many membrane proteins which may be inserted in the bilayer.

According to the third aspect of the present invention, there is provided a cell for use in the measurement of an electrical signal across a lipid bilayer, the cell comprising:

body elements defining two chambers, one of the chambers having an inlet opening for introduction of an aqueous solution;

a septum separating the two chambers, the septum comprising a membrane having an aperture capable of supporting a lipid bilayer arranged between the chambers; and electrodes in each chamber for receiving an electrical signal developed between the chambers, wherein the electrode in said one of the chambers being arranged in the flow path between the inlet opening and the aperture.

As a result of the location of the electrode in the flow path between the inlet opening and the aperture, when an aqueous solution is introduced into the chamber through the inlet opening it contacts the electrode before reaching the aperture. This means that the electrode is wetted before the lipid bilayer is formed. When the electrode is wetted, there can occur a pertubation in the potential across the electrodes. If this occurs before the lipid bilayer is formed, then this causes no difficulty. However if the aqueous solution was to contact the electrode after reaching the bilayer, such a pertubation in the potential across the electrodes could occur after the lipid bilayer is formed. This risks rupturing the lipid bilayer.

According to the fourth aspect of the present invention, there is provided an electrochemical sensor cell for detection of an analyte by measurement of an electrical signal developed in the cell, wherein the cell is enclosed by a Faraday cage attached around the cell.

The Faraday cage reduces electrical interference with the electrical signals generated in the cell from ambient electromagnetic radiation. By attaching the Faraday cage to the cell, it is possible to provide a compact Faraday cage, avoiding the need for the cell to be accommodated in a separate Faraday cage which will be larger and inconvenient for the user.

The fourth aspect of the present invention is of particular benefit in a sensor system using a lipid bilayer, but is also more generally applicable to any sensor system which measures electrical signal.

The various aspects of the present invention are all applicable together and are indeed present in different aspects of a common embodiment described below. As such any of the features described above with reference to any of the aspects of the present invention may be used together in any combination.

To allow better understanding, an embodiment of the present invention will now be described by way of non-limitative example with reference to the accompanying drawings, in which:

FIG. 1 is a perspective view of a sensor system;

FIG. 2 is a perspective view of a cell of the sensor system;

FIG. 3 is a cross-sectional of the cell, taken along line III-III in FIG. 2;

FIG. 7 is a cross-sectional view of the cell similar to that of FIG. 3 but showing introduction of a sample;

FIG. 8 is an expanded, partial cross-sectional view of a cell containing gel with a gap between the gel and an aperture;

FIG. 9 is a is a cross-sectional of the cell of FIG. 7 showing further introduction of a gel into the test chamber, FIG. 10 is an expanded perspective view of the connector portion of the reader unit;

FIG. 11 is a perspective view of a rigid metal body connected to the reader unit;

FIG. 12 is a cross-sectional view of the rigid metal body, taken along line XII-XII in FIG. 11;

FIG. 13 is a cross-sectional view of the cell contained in a Faraday cage;

FIGS. 14 to 16 are diagrams of various forms of the electrical circuit in the reader unit; FIG. 18 is a graph of a bias voltage applied to the reader unit; and FIGS. 19 to 23 are graphs of the current signal generated in the cell during operation.

Figure 4:
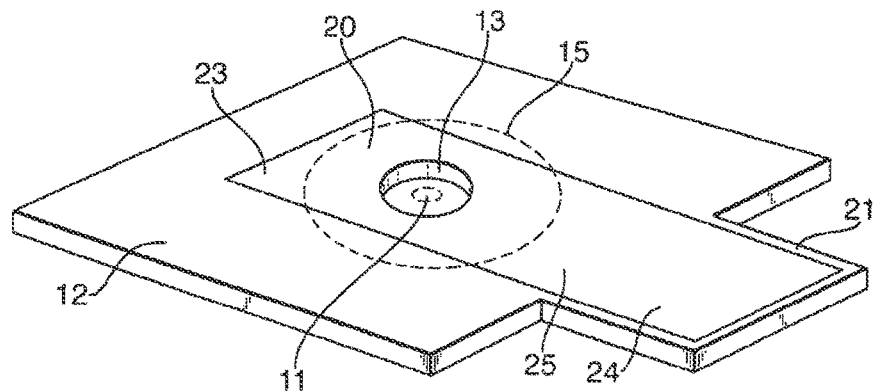
FIG. 4 is a perspective view of a support sheet of the cell in isolation.

A sensor system 1 is shown in FIG. 1 and comprises a cell 2 and an electrical reader unit 3 which may be connected together. In use, sensing using a lipid bilayer is formed in the cell 2 and an electrical current signal across the bilayer is monitored and interpreted by the reader unit 3. The sensor system 1 has been designed for use outside of a laboratory setting. Some examples include use in medicine for point of care testing (POCT), use in environmental protection for a field based test for pollutants, use for counter bioterrorism for the detection of explosives and chemical and biological agents at the "point of terror". Nonetheless, some of features of the sensor system 1 also make it advantageous for laboratory use.

The cell 2 has a construction allowing it to be mass-produced at a low cost, allowing it to be a disposable product. The cell 2 is easily connected and replaced in the reader unit 3. The reader unit 3 is sufficiently small to be hand-held and portable.

The cell 2 is shown in FIGS. 2 and 3 and will now be described in detail. The cell 2 has a layered construction formed from a stack of layers fixed together.

The cell 2 comprises a membrane 10 having an aperture 11 across which a lipid bilayer is supported in use. Although only a single aperture 11 is used in many applications, there may be plural apertures 11. The membrane 10 may be made of any material capable of supporting lipid bilayer across the aperture 11. Some examples include but are not limited to: a biaxial polycarbonate, PTFE, polyethylene, polypropylene, nylon, PEN, PVC, PAN, PES, polyimide, polystyrene, PVF, PET, aluminized PET, nitrocellulose, PEEK, or FEP. One factor in the choice of the material of the membrane 10 is the affinity to the lipid which affects the ease of bilayer formation. However the material of the membrane 10 has less significance when a pretreatment is used as described below. The choice of the material of the membrane 10 also affects the ease of formation of the aperture 11.

Similarly, the thickness of the membrane 10 is made sufficiently small to facilitate formation of the lipid bilayer across the aperture, typically being at most 25 µm, preferably being at most 10 µm thick, for example 5 µm or 6 µm. The thickness of the membrane 10 is typically at least 0.1 µm. The aperture 11 may in general be of any shape or size which it is capable of supporting a lipid bilayer, although it preferably has a restricted size as discussed further below.

The thickness of the membrane 10 is also dependent on the size of the aperture 11. As the aperture 11 decreases in size, the membrane 10 also needs to decrease in thickness in order to assist the formation of a lipid bilayer. Typically the thickness of the membrane 10 is no more than the minimum diameter of the aperture 1. Another factor is the electrical resistance of the membrane 10 which changes with the thickness. It is desirable that the resistance of the membrane 10 is sufficiently high relative to the resistance of the ion channel in a membrane protein inserted in the membrane 10 that the current flowing across the membrane 10 does not mask the current through the ion channel.

The membrane 10 is supported by two support sheets 12, provided on opposite sides of the membrane 10 and fixed thereto. As described further below, the membrane 10 and the support sheets 12 together form a septum 17. The support sheets 12 each have a window 13 which is aligned with the aperture 11 in the membrane 10 but is of larger size than the aperture 11 in order that the support sheets 12 do not interfere with the formation of a lipid bilayer across the aperture 11. The support sheets 12 have the function of supporting and strengthening the membrane 10 and may be made of any material suitable for achieving this purpose. Suitable materials include, but are not limited to: Delrin® (polyoxymethylene or acetal homopolymer), a polyester, eg Mylar® (biaxially-oriented polyethylene terephthalate (bo-PET)polyester film), PC, PVC, PAN, PES, polysulphone, polyimide, polystyrene, polyethylene, PVF, PET, FIFE, PEEK, or FEP The support sheets 12 are typically thicker than the membrane 10, having a thickness typically at least 0.1 μm, preferably at least 10 μm. The support sheets 12 are thinner than the bodies 14 described below, having a thickness typically at most 1 mm, preferably at most 0.5 mm.

The cell 1 further comprises two bodies 14 each fixed to one of the support sheets 12. The bodies 14 are each formed from a sheet of material having an aperture 15 extending therethrough. The apertures 15 in the bodies 14 are of larger area, parallel to the membrane 10, than the windows 13 in the support sheets 12 and are aligned therewith. Thus, the apertures 15 in the bodies 14 each define a respective chamber 16, the two chambers 16 being separated by the septum 17 formed by the membrane 10 and the support sheets 12 together, and the aperture 11 in the membrane 10 opening into each of the chambers 16.

The thickness of each body 14 is greater than the thickness of the support sheets 12 and are chosen to provide a desired volume for the chambers 16. In general, the bodies 14 may have any thickness, but typically the thickness of each body 14 is in the range from 1 m to 3 mm. Typically, for use in a disposable portable sensing system, the chambers 16 have a volume of 0.1 μl to 250 μl. However, a restricted thickness can be advantageous as described further below. The bodies 14 may be formed of any suitable material, for example silicone rubber.

The chambers 16 are closed by means of a respective closure sheet 18 which is fixed to the outer surface of the respective body 14 covering the aperture 15 formed therein. The closure sheet 18 may be formed from any material, but may for convenience be the same material as the support sheets 12.

The septum 17 including the membrane 10 is not electrically conductive and is designed to have a high electrical resistance. Consequently, in use, the only significant electrical connection between the two chambers 16 is by ionic conduction of an electrolyte solution in the chambers 16 through the aperture 11 in the membrane 10. Formation of a lipid bilayer across the aperture 11 blocks the aperture 11 creating a high-resistance electrical seal between the chambers 16. Insertion of a membrane protein which is an ion channel, for example a pore, restores the electrical connection between the two chambers 16 but only by ionic conduction through the membrane protein. Subsequently, binding events between an analyte and a membrane protein cause a characteristic interruption of the current flowing between the chambers under an applied electrical potential difference.

In order to detect and monitor such electrical signals, each of the chambers 16 is provided with an electrode 20 formed as part of a layer 23 of conductive material deposited on the surface of the respective support sheet 12 which is internal to the chamber 16. In particular, the electrodes 20 are illustrated in FIG. 4 which shows one of the support sheets 12 as viewed from the side internal to the adjacent chamber 16. In FIG. 4, the positions of the aperture 15 in the body 14 and the aperture 11 in the membrane 10 are shown in dotted outline. The conductive material of the electrodes 20 may be for example Ag/AgCl.

As shown in FIG. 4, the support sheets 12 each include a protruding portion 21 which extends beyond the periphery of the body 14. The layer 23 of conductive material which is deposited on the support sheet 12 to form the electrode 20 extends from the chamber 16 across the support sheet 12 to the protruding portion 21. Accordingly each layer 23 of conductive material forms not only an electrode 20 but also a contact 24 which is exposed on a connector portion 22, and a track 25 which electrically connects the contact 24 and the electrode 20. As described further below, the two protruding portions 21 of the two support sheets 12 together form a connector portion 22 for connecting the cell 2 to the reader unit 3, and the electrical signal received by the electrodes 20 in each chamber 16 is supplied to the reader unit 3 via the contacts 24.

In use, a sample solution is introduced into the chamber 16 on one side of the membrane 10. The chamber 16 which receives the sample solution will now be referred to as the test chamber 16-1 and the other chamber will now be referred to as the secondary chamber 16-2, although in many embodiments both chambers 16 will be identical in size and construction.

To allow introduction of the sample solution, the test chamber 16-1 may be provided with an inlet 30 or 32 using either one of the following two alternative arrangements.

Figure 5:
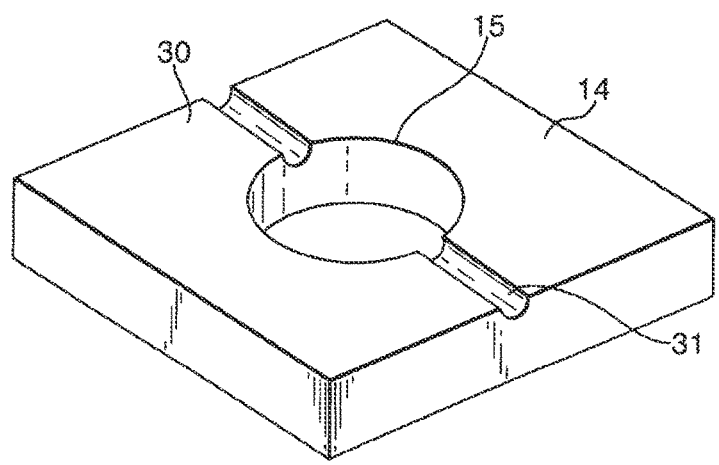
FIG. 5 is a perspective view of a body of the cell in isolation with a first arrangement for an inlet.

In the first inlet arrangement, the inlet 30 is formed in the body 14 as shown in FIG. 5. In particular, the inlet 30 is formed in one of the surfaces of the body 14 which may in general be either the inner or outer surface as a channel extending from the periphery of the body 14 to the aperture 15. The sample may be injected through the inlet 13, for example using a pipette or syringe. To allow exhaust of air in the chambers 16 displaced by the sample, the test chamber 16-1 is further provided with an exhaust outlet 31 having an identical construction to the inlet 30.

Figure 6:
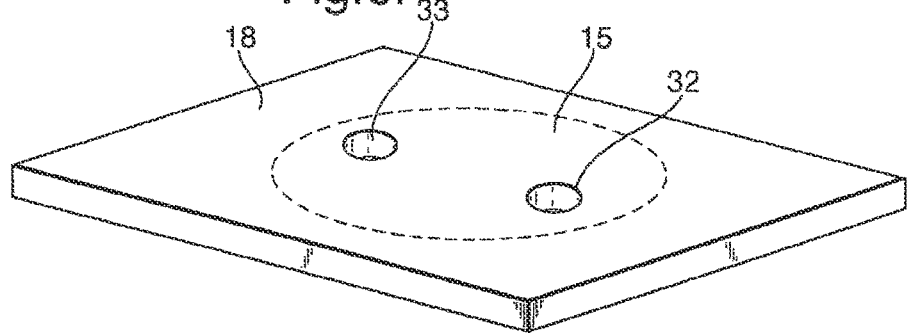
FIG. 6 is a perspective view of a cover sheet of the cell in isolation with a second arrangement for an inlet.

In the second inlet arrangement, the inlet 32 is formed in the closure sheet 18 as illustrated in FIG. 6. In particular, the inlet 32 is formed as a hole extending through the closure sheet 18 and aligned with the aperture 15 in the body 14 which defines the test chamber 16-1, as shown in dotted outline in FIG. 6. To allow exhaust of air in the chambers 16 displaced by the sample, the test chamber 16-1 is further provided with an exhaust outlet 33 having an identical construction to the inlet 32.

Such an inlet 30 or 32 may be provided with a closure, or may be omitted altogether by making a portion of the cell 2 of a material which allows penetration by a syringe for filling the test chamber 16-1.

As a result of the design of the electrode 20 as shown in FIG. 4, the electrode 20 is arranged in the flow path between the inlet 30 or 32 and the aperture 11. In other words, when an aqueous solution is introduced into the test chamber 16-1 through the inlet 30 or 32 it contacts the electrode 20 before reaching the aperture 11. This means that the electrode 20 is wetted before the lipid bilayer is formed, the formation of the bilayer being described in more detail below. When the electrode 20 is wetted, there can occur a pertubation in the potential across the electrodes 20 between the two chambers 16, derived from the reader unit 3. If this occurs before the lipid bilayer is formed, then this causes no difficulty. However if the aqueous solution was to contact the electrode 20 after reaching the bilayer, such a pertubation in the potential across the electrodes could occur after the lipid bilayer is formed and risk rupturing the lipid bilayer.

The secondary chamber 16-2 may, in use contains a buffer solution or a gel. The cell 2 may be supplied to users with the secondary chamber 16-2 already containing the buffer solution or gel. In this case, the secondary chamber 16-2 does not need an inlet 30 or 32 as described above. Alternatively the cell 2 may be supplied with the secondary chamber 16-2 empty. In this case, the user must introduce a buffer solution or gel into the secondary chamber 16-2. To facilitate this the secondary chamber 16-2 may also be provided with an inlet 30 or 32 as described above.

Thus the chambers 16 are closed except for an inlet 30 or 32 if provided. This contrasts with a conventional laboratory apparatus in which chambers on either side of an aperture are formed as recesses in a molded block which are open to the atmosphere. Use of closed chambers 16 has the advantage of reducing evaporation from the contents of the chambers 16. This in turn reduces the cooling of the contents which is important to maintain appropriate temperatures in the case of many membrane proteins which may be inserted in the bilayer.

The lipid bilayer will now be considered. A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer.

To facilitate formation of the lipid bilayer across the aperture 11 in the membrane 10, an internal surface of the test chamber 16-1 has a lipid deposited thereon. One or more lipids are deposited on one or more of any of the internal surfaces of the test-chamber 16-1. If the cell 2 is supplied with the secondary chamber 16-2 empty, then the lipid may be deposited in either or both of the test-chamber 16-1 and the secondary chamber 16-2.

Any method may be used to deposit the lipids on an internal surface of the cell 2. Suitable methods include, but are not limited to, evaporation or sublimation of a carrier solvent, spontaneous deposition of liposomes or vesicles from a solution, direct transfer of the dry lipid from another surface, drop coating, various printing techniques, spin-coating, painting, dip coating and aerosol application.

When aqueous solution is inserted into the cell 2, the sample rehydrates the lipids and forms a lipid/solution interface between the sample and the air in the test chamber 16-1 (or secondary chamber 16-2). This interface is subsequently moved across the aperture 11, either once or repeatedly, in order to form the lipid bilayer across the aperture 11.

This method of forming a lipid bilayer is described in more detail in a co-pending International application being filed simultaneously with this application and claiming priority from the same applications [J A Kemp & Co Ref: N.99662A; Oxford Nanolabs Ref: ONL IP 001] which is incorporated herein by reference. All the teachings of that application apply equally to the present invention.

The lipids are preferably dried. Even when dried to a solid state, the lipids will typically contain trace amounts of residual solvent. Dried lipids are preferably lipids that comprise less than 50 wt % solvent, such as less than 40 wt %, less than 30 wt %, less than 20 wt %, less than 15 wt %, less than 10 wt % or less than 5 wt % solvent.

The lipid bilayer can be formed from one or more lipids. The lipid bilayer can also contain additives that affect the properties of the bilayer.

Any lipids that form a lipid bilayer may be used. The dried lipids provided in the cell 2 are chosen such that a lipid bilayer having the required properties, such surface charge, ability to support membrane proteins, packing density or mechanical properties, is formed. The dried lipids can comprise a single lipid or plural different lipids. For example mammalian cell membranes, which are one type of membrane which it is desirable to model in the cell 2, comprise four major phospholipids, plus cholesterol, glycolipids, and various minor lipids. The likely number of lipids is from one to ten, but there could be more. The dried lipids may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipids can also be chemically-modified. The bead group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine.

The dried lipids typically comprise one or more additives that will affect the properties of the lipid bilayer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides. The dried lipid preferably comprises cholesterol and/or ergosterol when membrane proteins are to be inserted into the lipid bilayer.

In general, the dry lipid may be applied to any internal surface of the test chamber 16-1 (or secondary chamber 16-2). The lipid may be deposited on the septum 17 during manufacture after the septum 17 has been constructed by fixing together the membrane 10 and the support sheets 12 but before assembly of the septum 17 into the remainder of the cell 2. Alternatively the lipid may be deposited on the internal walls of the chamber 16 formed by the aperture 15 in the body 14 or the closure sheet 18, either before or after the body 14 is fixed to the closure sheet 18, but before assembly to the septum 17.

The deposition may be achieved by coating the septum 17 with a solution of the dried lipid dissolved in an organic solvent such as pentane and then subsequently allowing evaporation of the solvent, although other techniques could equally be applied.

The lipid bilayer is formed by introducing an aqueous solution into the test chamber 16-1. The aqueous solution covers both the internal surface on which the lipids are deposited and the aperture 11. For ease the test chamber 16-1 may be completely filled with the aqueous solution, although in principle it could be partially filled with the aqueous solution, as long as the both the lipids and the aperture 11 are covered with the aqueous solution.

The aqueous solution may cover the lipids and the aperture 11 in any order but preferably covers the lipids before the aperture 11. The inventors have shown that covering the lipids before the aperture 11 allows the lipid bilayer to form more easily. In particular, it allows the formation of a lipid bilayer across the aperture 11 following a single pass of the lipid/solution interface. The removal of the need to move the lipid/solution interface beck and forth past the aperture means that the method is simplified. It also means that there is no need for fluidics control in the device, thereby reducing its cost and size.

The design of the cell 2 and the position of the lipids may be chosen to determine the order in which the aqueous solution covers the lipids and aperture 11. For instance, if the lipids are to be covered first, the test chamber 16-1 is provided in which the lipids are positioned along the flow path between the inlet 32 through which the aqueous solution is introduced to the test chamber 16-1 and the aperture 11.

Any aqueous solution that collects the lipids from the internal surface and allows the formation of a lipid bilayer may be used. The aqueous solution is typically a physiologically acceptable solution. The physiologically acceptable solution is typically buffered to a pH of 3 to 9. The pH of the solution will be dependent on the lipids used and the final application of the lipid bilayer. Suitable buffers include, but are not limited, to phosphate buffered saline (PBS), N-2-Hydroxyethylpiperazine-N'-2-Ethanesulfonic Acid (HEPES) buffered saline, Piperazine-1,4-Bis-2-Ethanesulfonic Acid (PIPES) buffered saline, 3-(n-Morpholino)Propanesulfonic Acid (MOPS) buffered saline and Tris(Hydroxymethyl)aminomethane (TRIS) buffered saline. By way of example, in one implementation, the aqueous solution may be 10 mM PBS containing 1.0M sodium chloride (NaCl) and having a pH of 6.9.

The introduction of the aqueous solution collects the lipids from the internal surface. The immiscibility of the rehydrated lipids and the aqueous solution allows the formation of an interface between the lipids and the solution. The interface can be any shape and size. The interface typically separates a layer of lipids from the aqueous solution. The layer of lipids preferably forms on the top of the solution. The layer of lipid typically separates the solution from any air in the test chamber 16-1.

The lipid bilayer is formed as the interface moves past the aperture 11. The interface moves past the aperture 11 in such a way that the layer of lipids contacts the membrane material surrounding the aperture 11 and a lipid bilayer is formed. The interface can be at any angle relative to the membrane as it moves past the aperture 11. The interface is preferably perpendicular to the membrane as it moves past the aperture 11.

The interface may move past the aperture 11 as many times as is necessary to form the lipid bilayer. The interface moves past the aperture 11 at least once. The interface can move past the aperture 11 more than once, such as twice, three times or more.

If the aqueous solution covers the internal surface on which the lipids are deposited before the aperture 11, the lipid bilayer may form as the interface moves past the aperture 11 as the test chamber 16-1 fills. Hence, if the lipid bilayer can be formed by a single pass of the interface past the aperture 11, the step of moving the interface past the aperture 11 may be performed by the filling of the test chamber 16-1.

In other embodiments, it will be necessary to move the interface back and forth past the aperture 11. For instance, if the aqueous solution covers the aperture 11 before the lipids or covers the aperture 11 and lipids simultaneously, it may be necessary to move the interface back and forth past the aperture 11.

In addition, the membrane 10 is preferably pretreated by applying a chemical surface treatment to the membrane 10 around the aperture 11 prior to exposure to the test solution, to increase the affinity of the membrane 10 to lipids. The pretreatment makes the membrane 10 more compatible with the lipid and hence makes the lipid bilayer more likely to form. It has been experimentally shown that such pretreatment allows the lipid bilayer to form more easily and can reduce the number of passes of the lipid/solution interface past the aperture 11 which are needed. Such pretreatment also results in the formation of a lipid bilayer with increased stability. This increases the robustness of the lipid bilayer which is of great advantage when the sensor system 1 is used outside a laboratory setting where it may be disturbed by external forces.

The pretreatment may be any treatment that modifies the surface of the membrane surrounding the aperture to increase its affinity to lipids. The membrane is typically pretreated with long chain organic molecules in an organic solvent. Suitable long chain organic molecules include, but are not limited to, n-decane, hexadecane, hexadecane mixed with one or more of the lipids discussed below, iso-eicosane, octadecane, squalene, fluoroinated oils (suitable for use with fluorinated lipids), alkyl-silane (suitable for use with a glass membrane) and alkyl-thiols (suitable for use with a metallic membrane). Suitable solvents include but are not limited to: pentane, hexane, heptane, octane, decane, isoecoisane and toluene. The membrane might typically be pretreated with 0.1% to 50% (v/v) hexadecane in pentane or another solvent, preferably 2 µl of 1% (v/v) hexadecane in pentane or another solvent. The volume of hexadecane in pentane used is typically 0.1 µl to 10 µl. The protreatment may be mixed with any of the lipids discussed below, such as diphantytanoyl-sn-glycero-3-phosphocholine (DphPC), might be included at a concentration of 0.6 mg/ml.

Some specific pretreatments are set out in Table 1 by way of example and without limitation.

TABLE 1

| Pretreatment formulation | Volumes applied by capillary pipette |
|---|---|
| 0.3% hexadecane in pentane | 2x 1 µl |
| 1% hexadecane in pentane | 2x 0.5 µl; 2x 0.5 µl; 1 µl; 2x 1 µl; 2x 1 µl; 2 µl; 2x 2 µl; 5 µl |
| 3% hexadecane in pentane | 2x 1 µl; 2 µl |
| 10% hexadecane in pentane | 2x 1 µl; 2 µl; 5 µl |
| 0.5% hexadecane + 5 mg/ml DPhPC lipid in pentane | 5 µl |
| 1.0% hexadecane + 0.6 mg/ml DPhPC lipid in pentane | 2x 2x 0.5 µl |
| 1.5% hexadecane + 5 mg/ml DPhPC lipid in pentane | 2 µl; 2x 1 µl |

The precise volume of pretreatment substance required depends on the pretreatment both the size of the aperture 11, the formulation of the pretreatment, and the amount and distribution of the pretreatment when it dries around the aperture. In general increasing the amount of pretreatment (i.e. by volume and/or by concentration) improves the effectiveness, but too much pretreatment can block the aperture 11. As the diameter of the aperture 11 is decreased, the amount of pretreatment required also decreases. The distribution of the pretreatment can also affect effectiveness, this being dependent on the method of deposition, and the compatibility of the membrane surface chemistry.

The relationship between the pretreatment and the case and stability of bilayer formation is therefore complex, depending on a complex cyclic interaction between the aperture dimensions, the membrane surface chemistry, the pretreatment formulation and volume, and the method of deposition. The temperature dependent stability of the pretreated aperture further complicates this relationship. However, the pretreatment may be optimised by routine trial and error to enable bilayer formation immediately upon first exposure of the dr), aperture to the lipid monolayer at the liquid interface.

Although the pretreatment provides a beneficial effect, it is not essential.

In general the chambers 16 may be of any size. However, particular advantage is achieved by restricting the depth of the test chamber 16-1 in the direction perpendicular to the septum 17. This depth is controlled by selection of the thickness of the body 14. In particular, the depth is restricted to a level at which the surface tension of a sample solution introduced into the test chamber 16-1 prevents the liquid from flowing across the test chamber 16-1 and instead contains the liquid in part of the test chamber 16-1 across its area parallel to the septum 17. In this state, the liquid interface with the air in the chamber 16 extends across the depth of the chamber 16, perhaps with some meniscus forming depending on the relative pressures of the liquid and the air.

This effect is illustrated in FIG. 7 which shows a cell 2 in which the liquid sample 40 has been introduced into one side of the test chamber 16-1 through the inlet 30 or 32 (although for simplicity the inlet 30 or 32 is not shown in FIG. 7). As can be seen, instead of the liquid sample 40 falling under gravity to the lowest possible level in the chamber 16, surface tension holds the liquid interface 41 with the air in the chamber 16 extending across the depth of the chamber 16 between the septum 17 and the closure sheet 18. Thus, the interface 41 is generally perpendicular to the septum 17 and the aperture 11 except for the formation of a meniscus.

By applying pressure at the inlet 30 or 32 to introduce more liquid or to withdraw the liquid, the interface 41 may be moved in the direction of the arrow A along the chamber parallel to the septum 17 and hence across the aperture 11. Once the liquid sample 40 has rehydrated the dried lipid inside the chamber 16 the liquid interface 41 will support a layer of the lipid. Thus, such movement of the liquid interface 41 across the aperture 11 in the membrane 10 may be used to form a lipid bilayer.

A particular advantage of such a restricted depth for the chamber 16 is that the above-described effect of surface tension occurs irrespective of the orientation of the cell 2. Although the cell 2 is illustrated in FIG. 7 with the aperture 11 extending horizontally, the same effect occurs regardless of the orientation of the cell 2. Thus the above-described process of forming a lipid bilayer across the aperture 11 may be carried out with the cell 2 in any orientation. This reduces the degree of care needed by the user and enhances the ability to use the sensor system outside of a laboratory setting.

The cell 2 is easy to manufacture simply by cutting and affixing together the individual layers of the cell 2. For convenience the layers of the cell 2 are affixed by adhesive, although in principle some form of mechanical fixing could be used. Conveniently due to the use of a layered construction plural cells 2 or parts thereof may conveniently be manufactured together from a large sheet and subsequently cut out. As a result of these points, the cell 2 is capable of mass production at relatively low cost.

By way of example and without limitation, one particular manufacturing method will now be described in detail.

Firstly, a template for plural cells 2 is inkjet printed onto the release paper of adhesive-coated polyester A4 sized cards from which six rows of sixteen support sheets 12 are to be formed. The cards were Mylar polyester sheet (DuPont) of thickness 250 µm with a 467 MP self-adhesive coating of thickness 50 µm on one side. With the release-paper facing upwards, 4 mm diameter holes are punched in the cards on the template to provide the windows 13 of each support sheet 12 and any burring of the edges of the punched holes removed using a scalpel blade.

The layers 23 of conductive material are then stencil screen-printed onto the cards using a 60/40 composition silver/silver chloride paste (Gwent Electronic Materials Ltd.), and left overnight to dry at room temperature. The registration and electrical resistance of the layers 23 of conductive material is checked and the surface of the cards covered with a sheet of A4 paper, to keep the surface clean in subsequent stages of sensor production.

With the release paper side facing upwards, the cards are then cut using a guillotine lengthwise into the six rows of support sheets 12.

In this example the membranes 10 are formed from either a 6 µm thick biaxial polycarbonate film or a 5 µm thick PTFE film (Goodfellow Cambridge Ltd.). Prior to use the apertures 11 are formed as discussed below. The membrane 10 around the apertures 11 then receives a chemical pretreatment to facilitate the bilayer formation process. In this case, the pretreatment consists of 2 µl of 1% hexadecane in pentane applied to either side of the aperture by capillary pipette.

Once the pentane solvent had evaporated a 1 µl drop of aqueous protein solution (0.017 mg/ml w.t. α-HL) was applied near to one side of the aperture and dried.

Next the films are cut into strips, cleaned on both sides by rinsing with ethanol, and gently air-dried.

A tape-laying jig with a rubber coated veneer roller is used to roll the membrane film strips evenly over the self-adhesive of one half of the card rows. Care is taken to ensure that the film above the punched holes in the card remained flat and free from creases.

To complete the septums 17, the other half of the card rows are stuck back to back to sandwich the membrane film strips, with the punched holes carefully aligned on either side with the apertures 11. Then the strips are cut using a guillotine into septums 17 for individual cells 2.

In this example the body 14 is formed from a 2 mm thick solid silicone rubber sheet with self-adhesive coating on both sides. A large such sheet is cut into A4 sized sheets. An array of 12 mm diameter circular apertures 15 for respective cells 2 are formed by removal of the material of the sheet, in particular by hollow punching the spacer sheets. Chamber volumes as low as 56 µl have been produced by punching 6 mm diameter holes through the 2 mm thick spacer material.

The individual chambers 16 are then closed by sticking an A4 sized card of plain 250 µm thick Mylar polyester sheet (DuPont), which ultimately forms the closure sheets 18, to one side of the silicone rubber sheet. This sheet is then cut using a guillotine lengthwise into rows having the desired width of the body 14. Channels of width 1 mm, to form the inlet 30 and exhaust gas outlet 31 are then cut in the silicone rubber sheet material (but not through the backing card).

The interior of each chamber 16 is then coated with a solution of 4 µl of 10 mg/ml DPhPC lipid dissolved in pentane. The rows of lipid-loaded chambers are cut using a guillotine into individual chambers 16 according to the template and then bonded symmetrically to each side of the individual septums 17 to form cells 2.

The size and formation of the aperture 11 in the membrane 10 will now be considered further.

In general, the aperture 11 may be of any size capable of supporting a lipid bilayer. By way of comparison, the diameter of an aperture in a conventional laboratory apparatus is typically in the order of 30 µm to 150 µm and an aperture 11 of such a size may used in the present cell 2.

However, it has been appreciated that particular advantage may be achieved by restricting the size of the aperture 11. In particular, this has been found to increase the mechanical stability of the bilayers formed. The increased stability reduces the number of passes of the liquid interface supporting the lipid past the aperture necessary to allow formation of the bilayer. Furthermore, the increased stability increases the robustness of the bilayer and reducing the chances of the bilayer rupturing. This is of particular advantage when the sensor system 1 is used outside a laboratory setting where it may be subject to external forces.

The increased stability achieved by restricting the size of the aperture 11 has been experimentally demonstrated as follows.

A number of actual membranes 10 which have been tested are listed in Table 2 which sets out in the first column the thickness and material of the membrane 10 and in the second column the diameter and method of forming the aperture 11.

TABLE 2

| Membrane 10 | Aperture 11 |
|---|---|
| A  6 µm thick biaxial polycarbonate | 25 µm diameter spark generated |
| B  6 µm thick biaxial polycarbonate | 20 µm diameter laser drilled tapered |
| C  6 µm thick biaxial polycarbonate | 10 µm diameter laser drilled tapered |
| D  5 µm thick PTFE | 10 µm diameter spark generated |
| E  5 µm thick PTFE | 10 µm diameter laser drilled tapered |
| F  5 µm thick PTFE | 5 µm diameter laser drilled tapered |
| G  10 µm thick HD polyethylene | 15 µm diameter spark generated |
| H  4 µm thick Polypropylene | 15 µm diameter spark generated |
| I  25 µm thick Nylon (6,6) | 20 µm diameter spark generated |
| J  1.3 µm thick PEN | 30 µm diameter spark generated |
| K  14 µm thick conductive polycarbonate | 30 µm diameter spark generated |
| L  7 µm thick PVC | 20 µm diameter laser drilled |

The apertures 11 which are sparked-generated were produced by a spark generating device which comprises an adjustable high voltage generator that charges a storage capacitor, with feedback control. The storage capacitor is then switched to discharge into a high voltage transformer coil to rapidly produce a large potential difference between the points of two electrodes attached to the transformer output. Dielectric breakdown between the electrode points results in a spark. The energy of the spark is controlled by switching the value of the storage capacitor (33 nF-300 nF), by adjusting the capacitor charging voltage (200 nV-500V), and by changing the distance between the output electrode points.

The polymer film from which a membrane 10 is subsequently cut is mounted flat on the sparking platform and the two output electrodes of the sparking device are positioned opposite each other, above and below the film.

To form apertures 11 of small diameter the spark energy is minimised by choosing the lowest storage capacitor and lowest charging potential that can create a spark that penetrates through the film, and by controlling the dielectric resistance between the two electrodes. For example, decreasing the thickness of the membrane film enabled the use of lower energy sparks and produced smaller apertures, such that it was possible to create apertures in the range 5 µm-10 µm diameter in PTFE film of 5 µm thickness. Further control of the aperture 11 diameter could easily be introduced through limiting the sparking energy by gating the discharge after detecting the onset of dielectric breakdown.

The laser-generated apertures 11 were produce by laser drilling.

The morphology of the aperture 11 can been seen to vary with the material of the membrane 10 and method used to form the bilayer. For example, with biaxial polycarbonate film, the spark generated apertures 11 were elliptical while the laser drilled apertures 11 were mostly circular. Similarly the spark generated apertures 11 generally had a uniform cross-section while the laser drilled apertures 11 generally a cross section which tapered through the thickness of the membrane 10.

The regularity of the inside edge of the aperture 11 is also sensitive to the material of the membrane 10, the thickness of the membrane 10, and the method of formation of the aperture 11. This is expected to impact on the stability of bilayer formation at the aperture.

However in all cases irrespective of the method of formation of the aperture 11, it is apparent that restricting the diameter of the aperture 11 results in increasing the stability of the bilayers, in fact to a dramatic degree. For example with an aperture 11 of diameter 10 μm the cell 2 can firmly knocked against the table or disconnected from the reader unit 3 and carried by hand without breaking the bilayer. This is of significant advantage in the context of use of the sensor system 1 outside the laboratory setting.

For these reasons it is preferred that the aperture 11 has a restricted diameter, say of 20 μm or less in at least one dimension. The aperture 11 may have such a restricted diameter in all dimensions, but the advantage of increased stability is achieved provided the aperture 11 is relatively small in one dimension, even if the aperture 11 is longer in another dimension.

The work described above demonstrates that apertures 11 of small diameter may be formed using cheap off-the-shelf materials and processes adaptable for mass production. Nonetheless, the choice of materials for the membrane 10 and methods capable of generating the apertures 11 is considerably more extensive than those considered above.

As mentioned above, in one type of cell 2, the secondary chamber 16-2 may contain a gel 50 as shown for example in the cell 2 of FIG. 7. In particular, the gel 50 extends across the aperture 11 in the membrane 10. The presence of the gel acts to physically support a lipid bilayer formed across the aperture 11. As a result, the gel 50 assists the formation of the lipid bilayer and furthermore provides the lipid bilayer with increased stability. Both of these advantages are significant in the context of using the sensor system 1 in a non-laboratory setting, because it makes the sensor system 1 easier to use and also more robust against external forces of the type which may disturb the sensor system 1 in normal use. In addition, the gel 50 may act as a matrix for controlling the supply of molecules to the lipid bilayer.

In order to support the lipid bilayer, the gel 50 may fill the secondary chamber 16-2 such that the gel 50 contacts the membrane 10. This case is illustrated in FIG. 7. In this case, the gel 50 may directly support the lipid bilayer formed across the aperture 11. This is preferred in order to improve bilayer formation and stability.

However, in an alternative illustrated in FIG. 8, there may remain a gap 51 between the gel 50 and the membrane 10. In this case, the gel 50 may still support the lipid bilayer formed across the aperture 11 by acting through a solution occupying the gap 51, although this effect will reduce as the size of the gap 51 increases. The presence of the gap 51 means that a wider variety of materials can be used to make the gel 50, including ionically non-conductive materials.

The gel 50 may be ionically conductive and indeed this is necessary if the gel 50 directly contacts the lipid bilayer. In this case the gel 50 may be for example a hydrogel. Suitable ionically conductive gels include, but are not limited to, agarose polyacrylimide gel, Gellan™ gel or Carbomer™ gel. Particular gels which have been used are 5% agarose doped with NaCl or Signs Gel (Parker Laboratories Inc.). In one case agarose gel 50 was made using 10 mM PBS to which 1M NaCl had been added. The gel 50 was melted and then injected in the chamber 16 where it solidified upon cooling.

It has been discovered that when one chamber 16 of the cell 2 is filled with a gel 50, formation of a lipid bilayer was possible by moving the liquid interface 41 carrying a lipid monolayer past the aperture 11 on only one side of the aperture 11, as opposed to both sides of the aperture 11 as more commonly performed in the Montal & Muller method. Further, bilayers could be formed with or without pretreatment of the membrane 10 by this method. However considerably more attempts were required without the pretreatment. Pretreating only the top side of the membrane 10 was found to be sufficient for reproducible bilayer formation. Being able to apply the pretreatment to only one side of the membrane 10 greatly simplifies the manufacturing process.

The cell 2 may be provided to the user with the secondary chamber 16-2 already containing the gel 50. This improves the ease of use of the cell 2 because no filling the secondary chamber 16-2 is necessary by the user.

Each of the features described above of (1) restricting the size of the aperture 11, (2) use of a pretreatment and (3) use of a gel 50 assist the formation of a lipid bilayer across the aperture 11 in the membrane 10. In particular, this reduces the number of times in which the interface 41 carrying a lipid monolayer must be moved past the aperture 11 in order to form the bilayer. This improves the ease of use of the cell 2.

In fact, in actual embodiments of the cell 2 employing each of features (1) to (3) there has been demonstrated reliable formation of lipid bilayer on a single pass of the liquid interface 41 pass the aperture 11. This is of significant advantage because it means that the lipid bilayer may be formed across the aperture 11 simply on insertion of the test solution 40 into the cell 2, for example using a pipette or a syringe. This means that the user does not need to repeatedly move the liquid interface 41 back and fourth across the aperture 11 whilst monitoring the formation of the lipid bilayer, and so the required user skill level is greatly reduced. Furthermore, it is not necessary to employ any complicated fluidics control to so move the liquid interface 41.

The use of the sensor system 1 to provide sensing will now be considered. The sensing is based on monitoring of the electrical current signal developed between the chambers 16 as received by the electrodes 20. This signal varies in dependence on phenomenum occurring at the lipid bilayer. The lipid bilayer may be used as a biosensor to detect the presence of a range of analytes. Most common uses involve insertion of a membrane protein into the lipid bilayer. Typically the membrane protein is an ion channel such as a pore. For example the sensor system 1 may then be used to performs stochastic sensing to detect the presence or absence of an analyte or stimulus which affects an electrical signal measured across the lipid bilayer, typically the current flowing across the lipid bilayer. Similarly, the sensor system 1 may be used to detect the presence or absence of a membrane protein which is thus itself the analyte. The lipid bilayer may also be used for in vitro investigation of membrane proteins by single-channel recording. The lipid bilayer preferably contains membrane protein and is used to detect the presence or absence of a molecule or stimulus using stochastic sensing. The lipid bilayer may be used for a range of other purposes, such as studying the properties of molecules known to be present (eg DNA sequencing or drug screening), or separating components for a reaction.

In types of sensing involving an insertion of a membrane protein into the lipid bilayer, it is necessary to introduce the membrane protein into the cell. In principle, this may be performed by the user of the cell 2, but advantageously the membrane protein is already provided in the cell in a manner in which it spontaneously inserts into the lipid bilayer after formation thereof. This avoids the need for the user to take steps to actively cause insertion of the membrane proteins, for example by introduction of the membrane proteins into the solution surrounding the bilayer. This reduces the required user skill level. There may be one or more different membrane proteins.

In one technique, the membrane proteins may be deposited, preferably dried, on an internal surface of one or both of the chambers 16. In this case, the membrane proteins are used in a similar manner to the deposited lipids. The membrane proteins spontaneously insert into the lipid bilayer following the introduction of the aqueous solution, for example the sample, which rehydrates and collects the dried membrane protein. The inventors have shown that membrane proteins will spontaneously insert into the lipid bilayer following their removal from an internal surface of the cell 2 by the aqueous solution. This avoids the need to actively insert the membrane proteins into the lipid bilayer by introducing the proteins into the solution surrounding the bilayer or physically carrying the protein through the solution to the bilayer. Again, this simplifies the use of the cell 2 as well as removing the need for wet storage of the proteins and the need for automation.

The membrane protein may be provided on any internal surface of the cell 2, which may be the same or different internal surface as the dried lipid. The dried lipid and the membrane proteins may be mixed together.

The lipids, the aperture 11 and the membrane proteins may be covered by the aqueous solution in any order, although as already discussed the aqueous solution preferably covers the lipids first. The design of the cell and the position of the membrane proteins may be chosen to determine the order in which the aqueous solution covers the lipids, the aperture 11 and the membrane proteins.

Any method may be used to deposit the dried membrane proteins on an internal surface of the cell 2. Suitable methods include, but are not limited to, drop coating, various printing techniques, spin-coating, painting, dip coating, aerosol application.

The membrane proteins are preferably dried. Even when dried to a solid state, the membrane proteins will typically contain trace amounts of residual solvent. Dried membrane proteins are preferably membrane proteins that comprise less than 20 wt % solvent, such as less than 15 wt %, less than 10 wt % or less than 5 wt % solvent. However the proteins are likely to be stabilised by addition of another molecule which holds water.

In another type of embodiment the gel 50 may hold the membrane proteins. In particular, the membrane proteins may be present within the gel 50 or on a surface of the gel 50, for example on the surface facing the aperture 11 in the case of there being a gap 51 between the membrane 10 and the gel 50. Once the lipid bilayer has formed, the membrane proteins then move from the gel 50 and spontaneously insert into the lipid bilayer.

Any membrane proteins that insert into a lipid bilayer may be provided. The membrane proteins may be naturally-occurring proteins and/or artificial proteins. Suitable membrane proteins include, but are not limited to, n-barrel membrane proteins, such as non-constitutive toxins, porins and relatives and autotransporters; membrane channels, such as ion channels and aquaporins; bacterial rhodopsins; G-protein coupled receptors; and antibodies. Examples of non-constitutive toxins include hemolysin and leukocidin. Examples of porins include OmpG, OmpA, or OmpF.

Examples of autotransporters include the NalP and His transporters. Examples of ion channels include the potassium channel from *Streptomyces lividans* (KcsA), the bacterial mechanosensitive membrane channel of large conductance (MscL), the bacterial mechanosensitive membrane channel of small conductance (MscS) and gramicidin. Examples of G-protein coupled receptors include the metabotropic glutamate receptor. Some other specific membrane proteins which may be used include: staphylococcal leukocidin; maltoporin; gramicidin channel; glutamate receptor, mechanosensitive channels, for example MscL or MscS; or NMDA receptor.

The membrane proteins preferably comprise α-hemolysin or a variant thereof. The α-hemolysin pore is formed of seven identical subunits (heptameric). The polynucleotide sequence that encodes one subunit of a-hemolysin is shown in SEQ ID NO: 1. The full-length amino acid (sequence of one subunit of a-hemolysin is shown in SEQ ID NO: 2. The first 26 amino acids of SEQ ID NO: 2 correspond to the signal peptide. The amino acid sequence of one mature subunit of a-hemolysin without the signal peptide is shown in SEQ ID NO: 3. SEQ ID NO: 3 has a methionine residue at position 1 instead of the 26 amino acid signal peptide that is present in SEQ ID NO: 2.

A variant is a heptameric pore in which one or more of the seven subunits has an amino acid sequence which varies from that of SEQ ID NO: 2 or 3 and which retains pore activity. 1, 2, 3, 4, 5, 6 or 7 of the subunits in a variant a-hemolysin may have an amino acid sequence that varies from that of SEQ ID NO: 2 or 3. The seven subunits within a variant pore are typically identical but may be different.

The variant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO: 2 or 3, a variant will preferably be at least 50% homologous to that sequence based on amino acid identity. More preferably, the subunit polypeptide is at least 80%, at least 90%, at least 95%, at least 98%, at least 99% homologous based on amino acid identity to the amino acid sequence of SEQ ID NO: 2 or 3 over the entire sequence.

Amino acid substitutions may be made to the amino acid sequence of SEQ ID NO: 2 or 3, for example a single amino acid substitution may be made or two or more substitutions may be made. Conservative substitutions may be made, for example, according to Table 3, wherein amino acids in the same block in the second column and preferably in the same line in the third column may be substituted for each other.

TABLE 3

| NON-AROMATIC | Non-polar | G A P |
| | | I L V |
| | Polar - uncharged | C S T M |
| | | N Q |
| | Polar - charged | D E |
| | | H K R |
| AROMATIC | | H F W Y |

Non-conservative substitutions may also be made at one or more positions within SEQ ID NO: 2 or 3, wherein the substituted residue is replaced with an amino acid of markedly different chemical characteristics and/or physical size. One example of a non-conservative substitution that may be made is the replacement of the lysine at position 34 in SEQ ID NO: 2 and position 9 in SEQ ID NO: 3 with cysteine (i.e. K34C or K9C). Another example of a non-conservative substitution that may be made is the replacement of the asparagine residue at position 43 of SEQ ID NO: 2 or position 18 of SEQ ID NO: 3 with cysteine (i.e. N43C or N17C). The inclusion of these cysteine residues in SEQ ID NO: 2 or 3 provides thiol attachment points at the relevant positions. Similar changes could be made at all other positions, and at multiple positions on the same subunit.

One or more amino acid residues of the amino acid sequence of SEQ ID NO: 2 or 3 may alternatively or additionally be deleted. Up to 50% of the residues residues may be deleted, either as a contiguous region or multiple smaller regions distributed throughout the length of the amino acid chain.

Variants can include subunits made of fragments of SEQ ID NO: 2 or 3. Such fragments retain their ability to insert into the lipid bilayer. Fragments can be at least 100, such as 150, 200 or 250, amino acids in length. Such fragments may be used to produce chimeric pores. A fragment preferably comprises the 8-barrel domain of SEQ ID NO: 2 or 3.

Variants include chimeric proteins comprising fragments or portions of SEQ ID NO: 2 or 3. Chimeric proteins are formed from subunits each comprising fragments or portions of SEQ ID NO: 2 or 3. The ß-barrel part of chimeric proteins are typically formed by the fragments or portions of SEQ ID NO: 2 or 3.

One or more amino acid residues may alternatively or additionally be inserted into, or at one or other or both ends of, the amino acid sequence SEQ ID NO: 2 or 3. Insertion of one, two or more additional amino acids to the C terminal end of the peptide sequence is less likely to perturb the structure and/or function of the protein, and these additions could be substantial, but preferably peptide sequences of up to 10, 20, 50, 100 or 500 amino acids or more can be used. Additions at the N terminal end of the monomer could also be substantial, with one, two or more additional residues added, but more preferably 10, 20, 50, 500 or more residues being added. Additional sequences can also be added to the protein in the trans-membrane region, between amino acid residues 119 and 139 of SEQ ID NO: 3. More precisely, additional sequences can be added between residues 127 and 130 of SEQ ID NO: 3, following removal of residues 128 and 129. Additions can be made at the equivalent positions in SEQ ID NO: 2. A carrier protein may be fused to an amino acid sequence according to the invention.

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

The membrane proteins can be labelled with a revealing label. The revealing label can be any suitable label which allows the proteins to be detected. Suitable labels include, but are not limited to, fluorescent molecules, radioisotopes, e.g. 125I, 35S, enzymes, antibodies, polynucleotides and linkers such as biotin.

The membrane proteins may be isolated from an organism, such as Staphylococcus aureus, or made synthetically or by recombinant means. For example, the protein may be synthesized by in vitro translation transcription. The amino acid sequence of the proteins may be modified to include non-naturally occurring amino acids or to increase the stability of the proteins. When the proteins are produced by synthetic means, such amino acids may be introduced during production. The proteins may also be modified following either synthetic or recombinant production.

The proteins may also be produced using D-amino acids. In such cases the amino acids will be linked in reverse sequence in the C to N orientation. This is conventional in the art for producing such proteins.

A number of side chain modifications are known in the art and may be made to the side chains of the membrane proteins. Such modifications include, for example, modifications of amino acids by reductive alkylation by reaction with an aldehyde followed by reduction with NaBH4, amidination with methylacetimidate or acylation with acetic anhydride.

Recombinant membrane proteins can be produced using standard methods known in the art Nucleic acid sequences encoding a protein can be isolated and replicated using standard methods in the art. Nucleic acid sequences encoding a protein can be expressed in a bacterial host cell using standard techniques in the art. The protein can be introduced into a cell by in situ expression of the polypeptide from a recombinant expression vector. The expression vector optionally carries an inducible promoter to control the expression of the polypeptide.

The efficacy of the cell 2 described above has been experimentally demonstrated as will now be described.

The cell 2 was produced as described above. The pre-treatment of the membrane 10 used was hexadecane, prepared using a solution of 2 µl of 1% hexadecane in pentane. The membrane protein was Wild Type a-hemolysin (α-HL) and was dried onto the septum 17 by applying 1 µl of a 0.17 mg/ml solution. The lipid used was 1,2-diphytanoyl-sn-glycero-3-phosphocholine and was dried onto the septum 17 by applying 20 µl of a 10 mg/ml solution in pentane.

Subsequently, the cells 2 were re-hydrated by injecting a test solution of 10 mM Phosphate Buffered Saline solution, 1.0M NaCl, and 0.25 mM γ-cyclodextrin, at pH 6.9 into each chamber 16.

Control of the applied potential and monitoring of the resultant current signal between the electrodes 20 may be performed using the circuit of a conventional laboratory apparatus or using the reader unit 2 described below. Typically an electrical potential difference of +100 mV was applied between the two chambers 16 after the electrolyte solutions had been added.

The observed current signal was consistent with the expected process of bilayer formation, insertion of α-HL and stochastic binding events between the α-HL and γ-cyclodextrin. The actual nature of the signals is discussed below with reference to the reader unit 3.

From a product perspective, the cell 2 represents a significant advance in the commercial viability of sensing using a lipid bilayer. In particular the cell 2 provides the following significant advantages:

being quick and easy for a non-specialist user to set up and operate, requiring only a single application of the sample to the cell 2;

the ability to rapidly self-assemble a lipid bilayer from dry storage upon addition of the sample, spontaneously creating a bilayer containing pores without the need for automation, for immediate analyte measurement;

being constructed from cheap and simple materials using existing cost effective technologies for mass production;

chemically and mechanically stability both in storage and in operation, including a vibration insensitive lipid bilayer; and the capability of performing sensitive and specific single molecule detection, creating an electrical signal that is readily converted into a useful measurement.

A further technique which may be applied in the cell 2 is encapsulation of a lipid bilayer between two layers of gel as will now be described.

This technique uses a cell as shown in FIG. 7 in which the secondary chamber 16-2 contains a gel 50 prior to formation of the lipid bilayer across the aperture 11. The technique involves formation of the lipid bilayer and insertion of a membrane protein using the technique described above of simply filling the test chamber 16 with the test solution 40. Thus movement of the liquid interface 41 past the aperture 11 causes formation of the lipid bilayer across the aperture 11 and subsequent insertion of a membrane protein into the lipid bilayer occurs spontaneously. The formation of the lipid bilayer and insertion of the membrane protein may be monitored on the basis of the detectable signal generated between the chambers 16, as described above.

After formation of the lipid bilayer, a further gel 55 is introduced into the test chamber 16 through the inlet 30 or 32. The further gel 55 is ionically conductive. The further gel 55 may be of the same or different material from the gel 50.

The further gel 55 displaces the test solution 40, as shown in FIG. 9. Thus, the test solution 40 is ejected from the test chamber 16 through the exhaust outlet 31 or 33. The further gel 55 covers the lipid membrane and it has been shown that this may occur without damage to the lipid bilayer. Thus the further gel 55 in the test chamber 16 and the gel 50 in the secondary chamber 16-2 together encapsulates the lipid bilayer formed across the aperture 11.

Consequently, it has been demonstrated that the two gels 50 and 55 increase the stability of the lipid bilayer.

As a result of the further gel 55 being ionically conductive, even after encapsulation of the lipid bilayer between the two gels 50 and 55 allow the operation of the cell 2 as a sensor to continue. This has been demonstrated experimentally for the case of the membrane protein being α-HL and the analytes being α-cyclodextrin. For this system, binding events are evident in the generated electrical signal even after encapsulation of the lipid bilayer.

The reader unit 3 will now be described in detail.

The reader unit 3 has a connector portion 60 which is arranged to make a physical connection with the connector portion 24 of the cell 2. The connector portion 60 of the reader unit 3 is visible in FIG. 1 but is shown in expanded form in FIG. 10. In particular, the connector portion 60 consists simply of a pair of blocks 61 which are separated by a spacing designed to provide a tight fit for the connector portion 24 of the cell 2. Thus, the connector portion 24 of the cell 2 may be plugged into the connector portion 60 in between the blocks 61 by insertion of the cell 2 in the direction of arrow B, thereby providing mating between the connector portions 24 and 60.

In addition, respective contacts 62 and 63 are provided on each of the facing surfaces of the block 61 or the connector portions 60. The contacts 62 and 63 are simply pieces of metal, typically gold-plated to assist formation of good electrical contact. The contacts 62 and 63 may be sprung. When the connector portion 24 of the cell 2 is plugged into the connector portion 60 of the reader unit 3, the contacts 24 of the cell 2 make an electrical connection with the contacts 62 and 63 of the reader unit 3. The reader unit 3 includes an electrical circuit 90 described further below which is connected to the contacts 62 and 63. In this manner, the connection together of the cell 2 in the reader unit 3 allows the electrical signal generated between the chambers 16 to be supplied from the electrodes 20 to the reader unit 3.

There will now be described some alternatives for providing the cell 2 with a Faraday cage to produce electrical interference from ambient electrical magnetic radiation with the electrical signals generated in the cell 2 when it is connected to the reader unit 3. Two alternative approaches are as follows.

The first approach uses a rigid metal body 70 as the Faraday cage. The rigid metal body has an internal cavity 71 sufficient to accommodate the cell 2. At one end 72, the rigid metal body 70 is open and connected to the body 73 of the reader unit 3 so that the cavity 71 is aligned with the connection portions 60. In this way, the cell 2 is accommodated inside the cavity 71 when it is connected to the reader unit 3, as shown in FIG. 11.

However, rather than entirely enclosing the cell 2, the rigid metal body 70 has an aperture 74 facing the connector portion 60. The aperture 74 is of sufficient size to allow passage of the cell 2 when the cell 2 is connected to the reader unit 3. Therefore, an individual cell 2 may be connected to the reader unit 3 and replaced by another cell 3 by insertion through the aperture 74 without removal of the rigid metal body 70. It has been appreciated that surprisingly the presence of the aperture 74 does not prevent the operation of the rigid metal body 70 as a Faraday cage. In particular, this is because the aperture 74 may be of sufficiently small size that any electrical interference caused by electro magnetic radiation penetrating the aperture 74 is at a sufficient high frequency that it does not significantly degrade the quality of the electrical signal of interest. In particular, the aperture 74 of the rigid metal body 70 may have a maximum dimension (horizontally in FIG. 11) of 50 mm or less, preferably 20 mm or less.

The rigid metal body 70 also has a sample introduction hole 76 which is aligned with the inlet 30 or 32 when the cell 2 is connected to the reader unit 3. The sample introduction hole 76 allows the sample to be introduced into the cell 2 after the cell 2 has been connected to the reader unit 3. The sample introduction hole 76 is smaller than the aperture 74, typically having a maximum dimension of 5 mm or less. Thus the sample introduction hole 76 is also of sufficiently small size that any electrical interference caused by electro magnetic radiation penetrating the sample introduction hole 76 is at a sufficient high frequency that it does not significantly degrade the quality of the electrical signal of interest.

The second alternative approach is to provide a Faraday cage 75 fixed around the periphery of the cell 2, for example as shown in FIG. 13. In this case, the Faraday cage 75 entirely encloses the cell 2, except for the connector portion 24 which protrudes out of the Faraday cage 75. In this case, the Faraday cage 75 may be formed by a solid metal body. Alternatively, the Faraday cage 75 may be formed by a metal foil which has the advantage of being easy to manufacture, for example simply by adhering the metal foil to the exterior of the cell 2.

It is noted that the provision of a Faraday cage attached around the exterior of the cell 2 is equally applicable to other types of electrical sensor cell which are operative to detect an analyte by measurement of an electrical signal developed in the cell.

The reader unit 3 houses an electrical circuit 90 which will now be described in detail. The primary function of the electrical circuit 90 is to measure the electrical current signal developed across the electrodes 20 to provide a meaningful output to the user. This may be simply an output of the measured signal or may involve further analysis of the signal.

The electrical circuit 90 may take various different forms and some possible circuit designs are shown in FIGS. 14 to 16. In each design there are some common elements as follows.

The two contacts 62 and 63 of the connector portion 60 will be referred to as a reference contact 62 and a working contact 63. Although the electrodes 62 and 63 are physically the same, in operation the reference contact 62 provides a bias voltage potential relative to the working contact 63, whilst the working contact 63 is at virtual ground potential and supplies the current signal to electrical circuit 90.

A possible alternative which is not illustrated would be for the reference contact 62 to be held at ground and working contact 63 to be offset by the bias voltage.

The reader circuit 90 has a bias circuit 91 connected to the reference contact 62 and arranged to apply a bias voltage which effectively appears across the two contacts 62 and 63 and hence across the electrodes 20 of a cell 2 connected to the reader unit 3. The bias circuit 91 may take different forms as described below.

The reader circuit 90 also has an amplifier circuit 92 connected to the working contact 63 for amplifying the electrical current signal the electrodes 20 of the cell 2 and appearing across the two contacts 62 and 63. In each design of the electrical circuit 90, the amplifier circuit 92 consists of a first amplifier stage 93 and a second amplifier stage 94.

The first amplifier stage 93 is connected to the working electrode 63 and arranged to convert the current signal into a voltage signal in a first stage amplifier. It may comprise an electrometer operational amplifier configured as an inverting amplifier with a high impedance feedback resistor, of for example 500 MΩ, to provides the gain necessary to amplify the current signal which typically has a magnitude of the order of tens to hundreds of picoamps.

The second amplifier stage 94 is connected to the output of the first amplifier stage 93 and arranged to amplify and filter the voltage signal voltage. The second amplifier stage 94 provides sufficient gain to raise the signal to a sufficient level for processing in the microcontroller 95 described below. For example with a 500 MΩ feedback resistance in the first amplifier stage 93, the input voltage to the second amplifier stage 94, given a typical current signal of the order of 100 pA, will be of the order of 50 mV, and in this case the second amplifier stage 94 must provide a gain of 50 to raise the 50 mV signal range to 2.5V. If the signal contains frequencies beyond the bandwidth limit of the first stage then analogue filtering is provided in the second amplifier stage 94 to increase gain at frequencies beyond the first stage bandwidth limitation. The filtering results in a combined first and second stage frequency response with constant gain beyond the first stage limitation.

To save power, the analogue circuitry in the bias circuit 91 and the amplifier circuit 92 is shutdown when not being used. Each power rail is connected to bipolar PNP switching transistors for low leakage switching of the analogue circuitry.

Typically the signal will be unipolar, but if bipolar current signals are required the gain of the second amplifier stage 94 can be halved and a DC offset applied to the inverting input of the second amplifier stage 94 equal to half reference voltage value of the microcontroller 95.

The first design of the electrical circuit 90 shown in FIG. 14 and will now be described. This design is intended for a stand-alone battery-operated reader unit 3 with PC connectivity. In this case, the bias circuit 91 and the amplifier circuit 92 are connected to a microcontroller 95. The microcontroller 95 has a power control circuit 96 which supplies power from a battery. The microcontroller 95 incorporates an analog-to-digital converter 97 which receives the output of the amplifier circuit 92 and converts it into a digital signal. The analog-to-digital converter 97 may be of a successive approximation type or of a voltage-to-frequency type, both resulting in a digital word for each conversion. A sampling rate is chosen that is at least twice the bandwidth of the signal at the output of the second amplifier stage 94 to prevent aliasing.

In this case the analog-to-digital converter 97 is embedded on the same silicon die as the microcontroller 95, but it could alternatively be a separate circuit element.

The microcontroller 95 incorporates a microprocessor 98 which runs code to process and analyse the digital signal. The microcontroller 95 has a display 99 which is conveniently an LCD display, and on which the microcontroller causes display of the signal itself or other analysis results such as temporal results of the signal analysis.

The microcontroller 95 receives commands from a keypad 100. Of course other input and output devices could be used in addition to, or instead of, the display 99 and keypad 100, for example LEDs used as indicators or an audio generator 105.

The microcontroller 95 also has an interface 101 to provide data communication with another digital device, for example a computer. The interface 101 may be of any type, for example a UART interface. This allows the received signal to be supplied to another device for display, storage and/or further analysis.

The microcontroller 95 is connected to the bias circuit 91 as follows. The microcontroller 95 has a PWM generator 102 which generates a PWM (pulse width modulation) voltage waveform, that is a digital signal with fixed frequency but varying duty cycle. The PWM generator 102 is of conventional construction. Generally, an internal timer is set running to generate the PWM signal frequency and a register is loaded with the count at which the PWM output is switched and a comparator detects when the count is reached.

The bias circuit 91 includes a low-pass filter 103 connected to low-pass filter the PWM signal output by the PWM generator 102. The duty cycle of the PWM signal varies with time so that the output of the low-pass filter is the desired analog signal, which is the average voltage over one period of the PWM cycle. The PWM generator 102 built in this manner has a resolution equivalent to the smallest duty cycle change possible with the microcontroller 95. Bipolar outputs can be achieved by using a pair of PWM signals each connected to one of a pair of low pass filters 103 and one fed to the positive input and the other the negative input of a summing amplifier, this being shown in FIG. 14.

The bias circuit 91 further includes an output amplifier 104 for amplifying the output of the low-pass filter 103. In the case described above that a bipolar output is required, the output amplifier 104 is a summing amplifier arranged to subtract the output of one of the pair of low pass filters 103 from the other.

For systems requiring multiple or arrayed cells 2, the microcontroller 95 can be chosen with an embedded analogue multiplexer. In this case multiple analogue input circuits are required and the output of each second amplifier stage 94 is sampled by the analog-to-digital converter 97 through the multiplexer.

The second design of the electrical circuit 90 is shown in FIG. 15 and will now be described. This design is intended for a reader unit 3 which is a derivative of a standard Personal Digital Assistant (PDA) architecture. The second design is identical to the first design except that the microcontroller 95 interfaces with a PDA device 106 which is a conventional PDA. This allows the reader unit 3 to take advantage of the existing functionality of PDAs. The PDA device 106 may have input/output facilities based on a variety of protocols, such as universal connectors, Secure Digital cards (SD), Compact Flash cards (CF, CF2), Multi-Media cards (MMC), memory stick cards or SIM card. Such functionality may be used to provide a framework for the reader unit 2 to provide the functions of a large interactive display with key or touch entry and a rechargeable power source.

In this case, one option is for the connector portion 60, the amplifier circuit 92, the bias circuit 91 and the microcontroller 95 to be mounted within an electrical assembly shaped to fit in an SD card slot or other card format slot. This allows the reader unit 2 to be formed by an existing PDA device with the assembly fitted in a card slot.

The third design of the electrical circuit 90 is shown in FIG. 16 and will now be described. This design is intended for a reader unit 3 which is based on a data acquisition card 107 to be plugged into a computer 108 such as a desktop or laptop. This design is the simplest in terms of hardware development requiring only three amplifier stages and the data acquisition card. In this case the amplifier circuit 92 is arranged as described above, but the bias circuit 91 is simply formed by an inverting amplifier 109 supplied with a signal from a digital-to-analog converter 110 which may be either a dedicated device or a part of the data acquisition card 107 and which provides a voltage output dependent on the code loaded into the data acquisition card 107 from software.

The third design of the electrical circuit 90 shown in FIG. 16 may be modified to provide a multi-port reader system connected through a fast transport interface such as the Universal Serial Bus or Ethernet for the purpose of analysing many cells at once. In work involving drug-screening or an industrial manufacturing environment there is a need for multiple readers connected to a central computer for research, analysis and quality control. In this case the data acquisition card 107 is modified to provide the transport interface allowing multiple data streams into the computer.

The electrical circuit 90 may provide analysis of the received signal. Such analysis may be performed, for example, by programming one of the microprocessors in the electrical circuit, for example the microprocessor 98 in the microcontroller 95 or the PDA device 106 in the above described designs of the electrical circuit. In particular the analysis may involve interpretation of the electrical signal. As already described, the electrical signal is characteristic of the physical state of the cell 2. Accordingly, the state of the cell 2 can be detected from the electrical signal by the electrical circuit 90.

For example, when the cell 2 is used as described above, the following states each have a characteristic electrical signal which may be detected by the electrical circuit 90:

1) the chambers 16 in the cell 2 being dry;

2) the chambers 16 in the cell 2 containing an aqueous solution without a lipid bilayer being formed across the aperture 11 in the membrane 10;

3) a lipid bilayer being formed across the aperture 11 in the membrane 10 without a membrane protein being inserted therein;

4) a lipid bilayer being formed across the aperture 11 in the membrane 10 with a membrane protein being inserted therein without an analyte binding to the membrane protein; and 5) a lipid bilayer being formed across the aperture 11 in the membrane 10 with a membrane protein being inserted therein with an analyte binding to the membrane protein.

Such states may be detected based on predetermined thresholds or adaptive thresholds, which may be derived from scientific study of the membrane protein and physical system being used in the cell 2. On detection of such a state, the electrical circuit 90 then produces an output indicative of the detected state, for example by displaying the detected state on the display 99 or some other audio and/or visual output, or by outputting a signal indicative of the detected state, for example to a computer device connected thereto.

By detecting the continuous sequence of states (1) to (5) in order, the reader unit 2 may also monitor the correct performance of the sensing process to check and ensure that the cell 2 is operating correctly from the moment it is connected to the reader unit 3 until the end of the measurement assay. The reader unit 3 may apply a bias potential and continuously monitor the resultant signal. If the signal falls outside the expected levels showing a proper progress through the states (1) to (5), the reader unit 3 may output a signal reporting an error mode, or alternatively may perform an automated remediation.

As each state is detected the time duration of the state will be stored for subsequent or continuous statistical analysis. This may provide further information. For example, signals derived from single molecule binding events in or near multiple membrane protein channels will result in a time-varying current based on the number of binding events.

Another example is where the membrane protein includes a tether. Signals derived from either single or multiple binding events to either single or multiple tethers attached to single or multiple membrane protein channels will appear as noisy signals which become less noisy when the tether or tethers are bound to a target analyte. Each tether will have a binding site for the target analyte. These signals will be analysed with an algorithm to detect the reduction in noise and as each event is detected the time duration of the event or the time course of noise reduction will be stored for subsequent or continuous statistical analysis.

Figure 17:
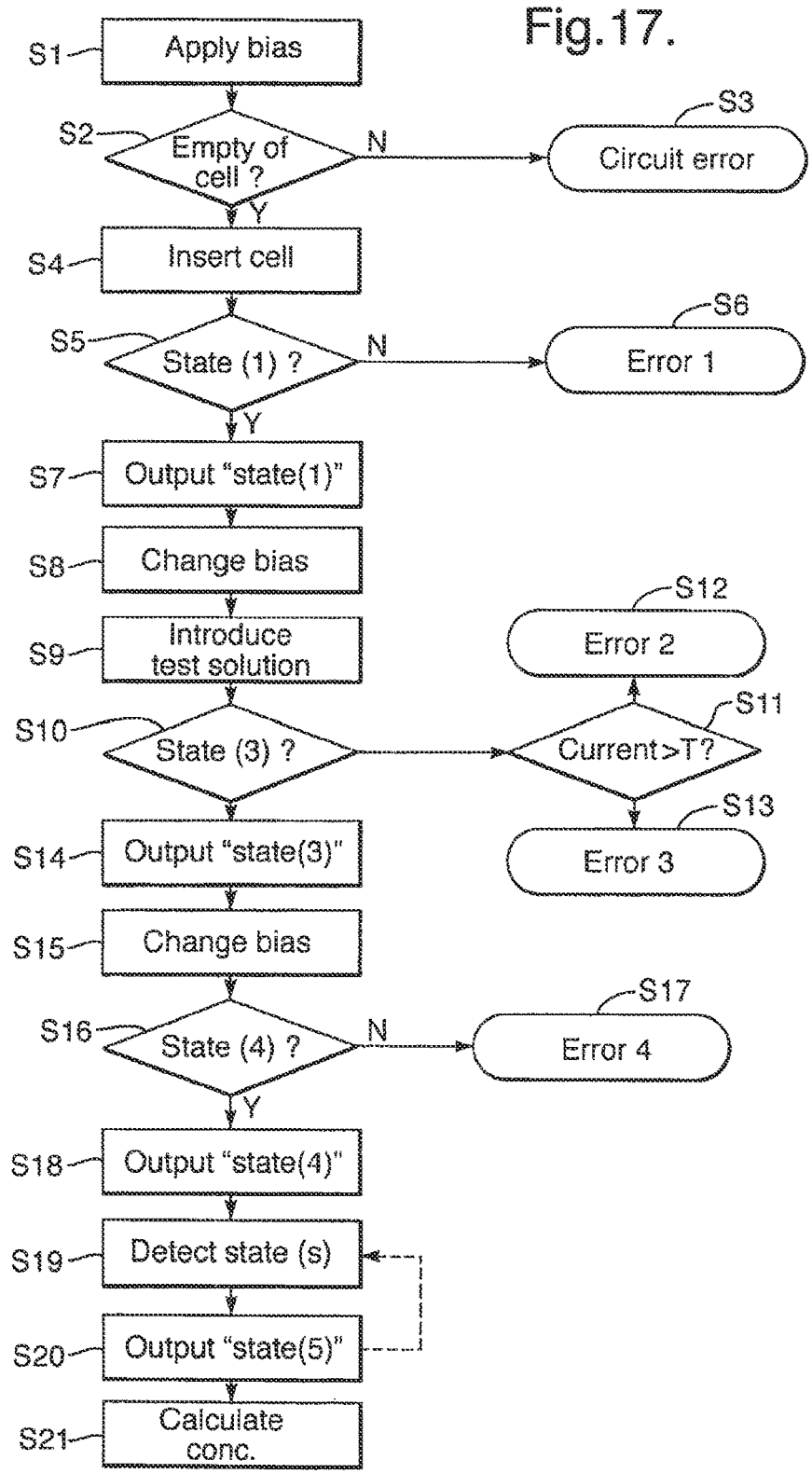
FIG. 17 is a flow chart of the operation of the reader unit.

There will now be described an actual example of the algorithm used to monitor of the state of the cell 2 in the case using the membrane protein α-HL to sense the presence of the analyte γ-cyclodextrin. The electrical circuit 90 performs the process as shown in FIG. 17.

In an initialisation step S1 performed before connection of the cell 2 to the reader unit 3, the electrical circuit 17 applies a bias voltage as shown in FIG. 18 having a waveform which is a 50 Hz triangular AC signal with 20 mV amplitude, superimposed on +100 mV DC potential.

In step S2 it is detected whether the received signal is representative of a current and impedance within the respective limits for the reader unit 3 in the absence of the cell 2. In the absence of the cell 2, the contacts 62 and 63 of the reader unit 3 behaves as a capacitor and produce a square wave current response to the applied triangular AC potential, as shown in FIG. 19. In particular the square wave has a 20 pA amplitude centred on 0 pA. This waveform is characteristic of normal operation of the electrical circuit 90 and so in step S2 it is detected whether this waveform is produced, within a reasonable margin. If not, then in step S3, the electrical circuit 90 outputs a signal indicate indicative of a circuit error. Otherwise in step S4, the user connects a cell 2 to the reader unit 3. The electrical circuit 90 may for example await a user input to indicate this.

Subsequently in step S5, there is detected state (1) that the chambers 16 in the cell 2 are dry. In this case, the expected signal is the same as that detected in step S2 except that the insertion of the cell 2 causes an increase, for example the order of 25%, in the amplitude of the resultant squarewave, for example to provide an amplitude of 27 pA. If state (1) is not detected, then in step S6 and there is output an error signal indicating malfunctioning of the cell 2.

Otherwise, in step S7 there is output a signal indicating state (1) and in step S8 the electrical circuit 90 changes the bias potential by removing the DC component, but maintaining the AC voltage of the waveform shown in FIG. 18. In step S9, the user introduces the test solution into the cell 2.

Figure 20:
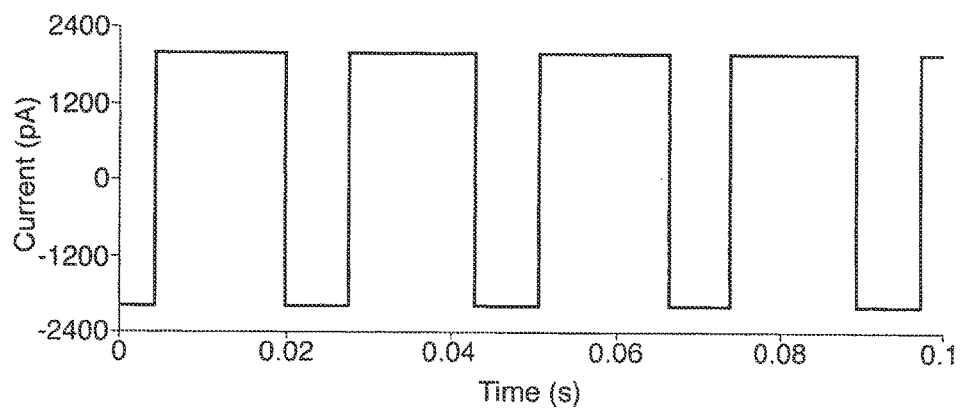

In this particular implementation, state (2) is not detected, but in step S10 there is detected state (3) of the lipid bilayer being formed across the aperture 11, as follows. In the absence of a lipid bilayer, the aperture 11 provides a conductive path between the electrodes 20 and so the cell 2 provides a current response. Typically the current saturates the amplifier, for example as shown in the typical response shown in FIG. 20.

Figure 21:
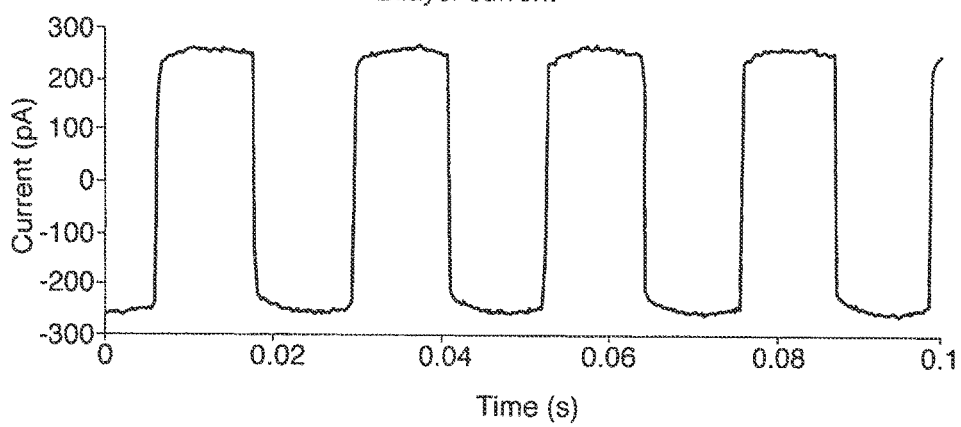

In contrast, formation of the lipid bilayer prevents flow of ionic current through the aperture 11 and so the cell 2 provides a capacitive response. As a result, the resultant current signal is a squarewave as shown in FIG. 21 typically having an amplitude of around 250 pA centred on 0 pA. State (3) is detected in step S10 by detecting a current signal showing this capacitive response. Typically the DC resistance is greater than 10GΩ.

If state (3) is not detected, then in step S11 the detected current is compared to a threshold and then depending on whether the threshold is exceed or not there is output one of two possible error signals in steps S12 and S13 which indicate the absence of bilayer formation.

However, if state (3) is detected in step S10, then in step S14 there is output a signal indicating that state (3) has been detected and in step S15 the bias voltage is changed by removing the AC waveform and instead applying a DC waveform.

Figure 22:
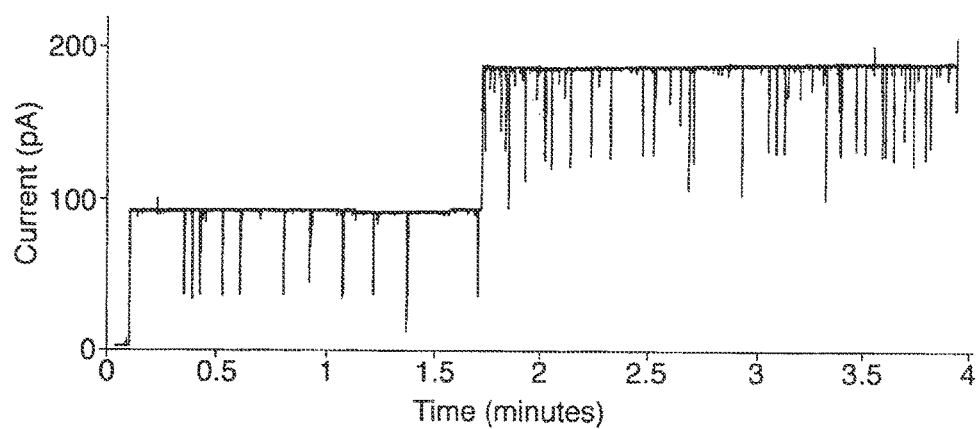

In step S16 there is detected state (4) of a membrane protein being inserted into the lipid bilayer formed across the aperture 11. This is detected by detection of the predictable step increases in the DC current response which occurs on insertion of the membrane protein due to the ionic current flowing through the ion channel. This is shown in FIG. 22 which shows the current increasing by a step of the order of 95 pA on insertion of single α-HL membrane protein. In this example, one such insertion occurs at around 0.1 minutes and a second insertion occurs at around 1.7 minutes. Since the electrical composition of the solution and the bias potential are known, the total current reflects the total number of membrane proteins inserted and this information may be determined and subsequently used to calibrate the assay calculations.

If state (4) is not detected within a reasonable period then there is output in step S17 an error signal indicating failure of insertion. Otherwise, in step S18 there is output a signal indicating that state (4) has been detected.

Figure 23:
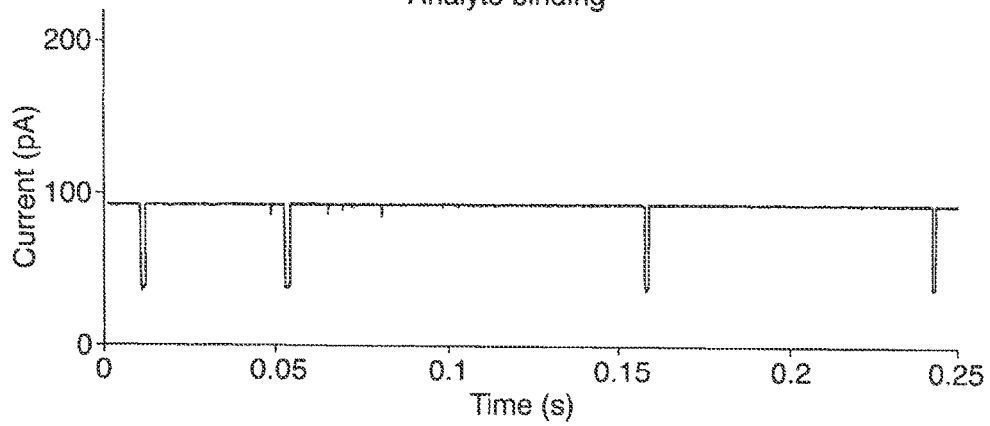

Thereafter, in step S19 there is detected state (5) of an analyte binding to the membrane protein. This may be detected as follows. When the analyte binds to the membrane protein this temporarily interrupts the ironic current passing through the ion channel causing a characteristic step decrease in the current. Prior knowledge of the analyte binding characteristics (eg current deflection and distribution in event duration) allows the electrical circuit 90 to identify the relevant binding events. An example of the current is shown in FIG. 23. The analyte γ-cyclodextrin causes a decrease in the current of the order of 60 pA. Four such binding events are evident in FIG. 23. The electrical circuit 90 detects these characteristic changes as binding events. A signal indicative of this is output in step S20. To detect successive binding events, steps S19 and S20 are repeated.

Finally in step S21 the concentration of the analyte α-cyclodextrin is calculated based on the kinetics of the measured analyte binding.

The invention claimed is:

1. A sensor system for measuring an electrical signal across a lipid bilayer, the sensor system comprising a cell and a portable electrical reader unit which are connectable together;

wherein the cell defines two chambers separated by a septum, the septum comprising a membrane having an aperture capable of supporting a lipid bilayer and arranged between the chambers, wherein the chambers each have a volume in the range from 0.1 µL to 250 µL, and a depth of at most 3 mm between the septum and a respective closure sheet for each chamber, such that surface tension of a liquid in the chamber contains the liquid across an area of the chamber parallel to the septum, and such that an interface of the liquid with air in the chamber extends across the depth of the chamber;

wherein the cell has electrodes formed in each chamber for receiving an electrical signal developed between the chambers, wherein the electrical reader unit has a reader circuit operative to measure an electrical signal developed between the chambers of the cell, and wherein the cell and the electrical reader unit are arranged to be connected together to provide electrical connection between the electrodes of the cell and the reader circuit of the electrical reader unit.

2. The sensor system according to claim 1, wherein the cell and the electrical reader unit have respective connector portions arranged to mate for connection together of the cell and the electrical reader unit, and the cell has contacts electrically connected to the electrodes and the electrical reader unit also has contacts electrically connected to the reader circuit, the contacts of the cell and the electrical reader unit being arranged to make electrical connection with each other on connection together of the cell and the electrical reader unit.

3. The sensor system according to claim 2, wherein the contacts of the cell and the electrical reader unit are provided on the connector portions of the cell and the electrical reader unit, respectively.

4. The sensor system according to claim 2, wherein the respective connector portions of the cell and the electrical reader unit have are arranged to mate by being plugged together.

5. The sensor system according to claim 1, wherein the aperture in the membrane has a diameter in at least one dimension which is 20 µm or less.

6. The sensor system according to claim 1, wherein the electrodes are deposited on the walls of each chamber.

7. The sensor system according to claim 1, wherein the membrane has a pretreatment effective to increase the affinity of the membrane to a lipid.

8. The sensor system according to claim 1, wherein one of the chambers contains a gel which extends across the aperture in the membrane.

9. The sensor system according to claim 8, wherein the gel is a hydrogel.

10. The sensor system according to claim 1, wherein one of the chambers has a lipid provided on an internal surface thereof.

11. The sensor system according to claim 1, wherein the electrical reader unit further comprises a rigid metal body having a cavity containing the connector portion of the electrical reader unit and being of sufficient size to accommodate the cell when connected to the electrical reader unit, the rigid metal body having an aperture which aperture faces the connector portion of the electrical reader unit and is of sufficient size to allow passage of the cell for connection of the cell to the electrical reader unit.

12. The sensor system according to claim 11, wherein the aperture of the rigid metal body has a maximum dimension of 50 mm or less.

13. The sensor system according claim 1, wherein the reader circuit comprises:

an amplifier for amplifying an electrical signal received at the contacts of the electrical reader unit;

an analog-to-digital converter for converting the amplified electrical signal into a digital signal; and a microprocessor for receiving and analysing the digital signal.

14. The sensor system according to claim 1, wherein the electrical reader unit includes a display and is operative to display the electrical signal measured by the reader circuit.

15. The sensor system according to claim 1, wherein the reader circuit is operative to interpret the electrical signal measured thereby by detecting one or more of the following states in the cell and producing an output indicative of the detected state, the states being:

1) the chambers in the cell being dry;
2) the chambers in the cell containing an aqueous solution without a lipid bilayer being formed across the aperture in the membrane;
3) a lipid bilayer being formed across the aperture in the membrane without a membrane protein being inserted therein;
4) a lipid bilayer being formed across the aperture in the membrane with a membrane protein being inserted therein without an analyte binding to the membrane protein; and
5) a lipid bilayer being formed across the aperture in the membrane with a membrane protein being inserted therein with an analyte binding to the membrane protein.

16. The sensor system according to claim 1, wherein the electrical reader unit further includes a bias circuit operative to provide a bias to the contacts of the electrical reader unit for supply to a cell connected to the electrical reader unit.

17. The sensor system according to claim 1, wherein the electrical signal is a current.

18. The sensor system according to claim 1, further comprising a bilayer supported by the aperture.

19. The sensor system according to claim 18, wherein the bilayer is a lipid bilayer.

20. The sensor system according to claim 18, wherein the bilayer contains an ion channel that connects the two chambers.

21. The sensor system according to claim 1, wherein the chambers each have a volume in the range from 56 µL to 250 µL.

* * * * *